(12) United States Patent
Gupta et al.

(10) Patent No.: US 10,434,149 B2
(45) Date of Patent: *Oct. 8, 2019

(54) SYNTHETIC PLATELETS

(71) Applicant: Case Western Reserve University, Cleveland, OH (US)

(72) Inventors: Anirban Sen Gupta, Cleveland, OH (US); Christa Pawlowski, Seven Hills, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 211 days.

This patent is subject to a terminal disclaimer.

(21) Appl. No.: 15/584,793

(22) Filed: May 2, 2017

(65) Prior Publication Data
US 2018/0071368 A1 Mar. 15, 2018

Related U.S. Application Data

(63) Continuation-in-part of application No. 14/826,387, filed on Aug. 14, 2015, now Pat. No. 9,636,383, which is a continuation of application No. 14/111,650, filed as application No. PCT/US2012/033444 on Apr. 13, 2012, now Pat. No. 9,107,845.

(60) Provisional application No. 61/475,039, filed on Apr. 13, 2011.

(51) Int. Cl.
| | |
|---|---|
| *A61K 38/39* | (2006.01) |
| *A61K 47/69* | (2017.01) |
| *A61K 9/48* | (2006.01) |
| *A61K 9/127* | (2006.01) |
| *C07K 14/745* | (2006.01) |
| *A61K 38/00* | (2006.01) |
| *A61K 38/17* | (2006.01) |
| *A61K 9/00* | (2006.01) |
| *A61K 38/36* | (2006.01) |
| *C07K 14/705* | (2006.01) |
| *C07K 14/78* | (2006.01) |
| *B82Y 5/00* | (2011.01) |

(52) U.S. Cl.
CPC ............ *A61K 38/39* (2013.01); *A61K 9/0019* (2013.01); *A61K 9/127* (2013.01); *A61K 9/1271* (2013.01); *A61K 9/4825* (2013.01); *A61K 38/00* (2013.01); *A61K 38/177* (2013.01); *A61K 38/1774* (2013.01); *A61K 38/36* (2013.01); *A61K 47/6911* (2017.08); *A61K 47/6929* (2017.08); *C07K 14/705* (2013.01); *C07K 14/745* (2013.01); *C07K 14/78* (2013.01); *B82Y 5/00* (2013.01)

(58) Field of Classification Search
None
See application file for complete search history.

(56) References Cited

U.S. PATENT DOCUMENTS

| | | | |
|---|---|---|---|
| 9,107,845 | B2 | 8/2015 | Gupta et al. |
| 2007/0059376 | A1 | 3/2007 | Takeoka et al. |
| 2008/0213369 | A1 | 9/2008 | Gyongyossy-Issa et al. |

FOREIGN PATENT DOCUMENTS

| | | | |
|---|---|---|---|
| WO | 2010/008792 A1 | | 1/2010 |
| WO | WO2010/008792 | * | 1/2010 |

OTHER PUBLICATIONS

Gilbert et al. (Biochemistry. Mar. 7, 1995;34(9):3022-31) (Year: 1995).*
Cejas et al. (Bioconjug Chem. Jul.-Aug. 2007;18(4):1025-7) (Year: 2007).*
Huang et al. (Biomaterials 29 (2008) 1676e1685) (Year: 2008).*
Lee, ImShik, et al., "Force measurements on the molecular interactions between ligand 1 (RGD) and human platelet allbβ3 receptor system", Surface Science 491 (2001) 433-443.
Mo, Xio, et al. "Nanparticle-Assisted visualization of binding interaction between collagen mimetic peptide and collagen fivers", Angew. Chem. Int. Ed. 2006, 45, 2267-2270.
Nogami, Keiji, Relationship between the binding sites for von Willebrand Factor, Phospholipid, and Human Factor VIII C2 Inhibitor Alloantibodies with in the Factor VIII C2 Inhibitor Alloantibodies with the factor VIII C2 Domain, May 2007, vol. 85, Issue 4, pp. 317-322.
Gilbert et al., Membrane-Binding Peptide from the C2 Domain of Factor VIII Forms an Amphipathic Structure As Determined by NMR Spectroscopy, Biochemistry 1995,34, 3022-3031.
Cejas et al, Nanoparticles That Display Short Collagen-Related Peptides. Potent Stimulation of Human Platelet Aggregation by Triple Helical Motifs, Bioconjugate Chem. 2007,18,1025-1027.
Huang et al, Affinity manipulation of surface-conjugated RGD peptide to modulate binding of liposomes to activated platelets, Biomaterials 29 (2008) 1676-1685.
Pugh, N., et al., "Synergism between platelet collagen receptors defined using receptor-specific collagen-mimetic peptide substrata in flowing blood", Blood, vol. 115, No. 24, pp. 5069-5079,Mar. 29, 2010.

(Continued)

*Primary Examiner* — Sergio Coffa
(74) *Attorney, Agent, or Firm* — Tarolli, Sundheim, Covell & Tummino LLP

(57) ABSTRACT

A method of promoting hemostasis in a subject in need thereof includes administering to the subject a biocompatible flexible nanoparticle that includes an outer surface and a plurality of peptides conjugated to the surface, wherein the peptides include a plurality of von Willebrand factor-binding peptides (VBPs), collagen-binding peptides (CBPs) and an active platelet GPM-Ma-binding peptides (GBPs).

10 Claims, 28 Drawing Sheets

Specification includes a Sequence Listing.

(56) References Cited

OTHER PUBLICATIONS

Ravikumar, M., et al., "Peptide-Decorated Liposomes Promote Arrest and Aggregation of Activated Platelets under flow on Vascular Injury Relevant Protein Surfaces in Vitro", Biomacromolecules, vol. 13, pp. 1495-1502, Apr. 3, 2012.

Srinivasan, R., et al., "In vitro and in vivo Platelet targeting by cyclic RDG-modified liposomes", Journal of Biomedical Materials Research Part A., vol. 93A, pp. 1004-1015, Sep. 9, 2009.

* cited by examiner

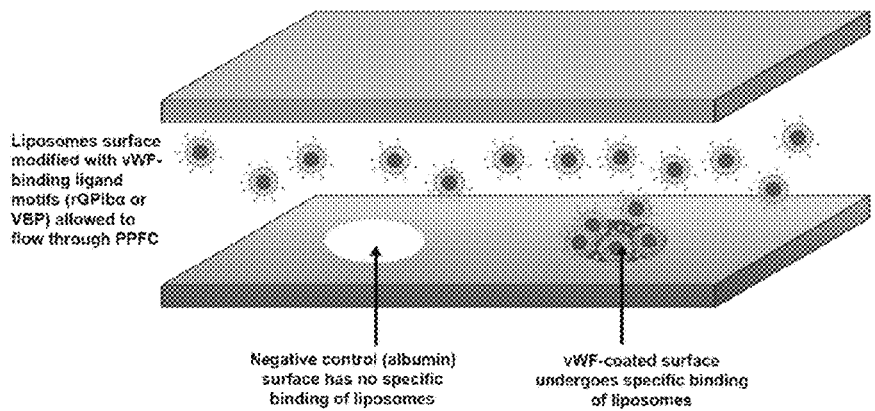
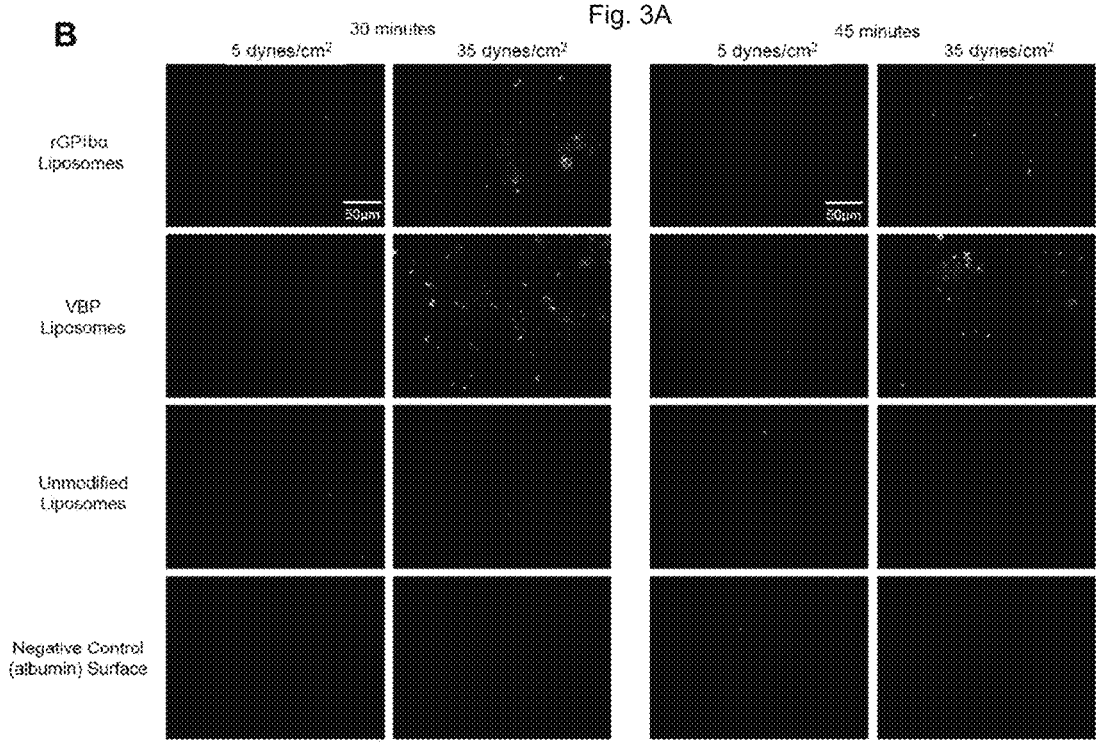
Fig. 3A
Fig. 3B

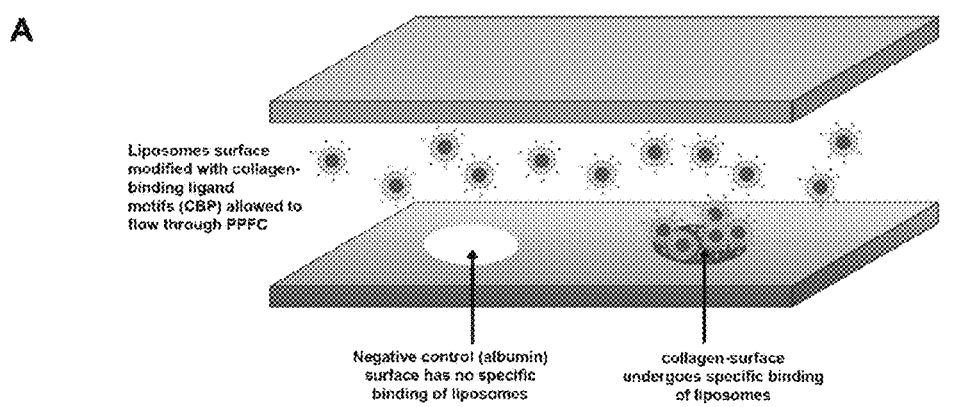
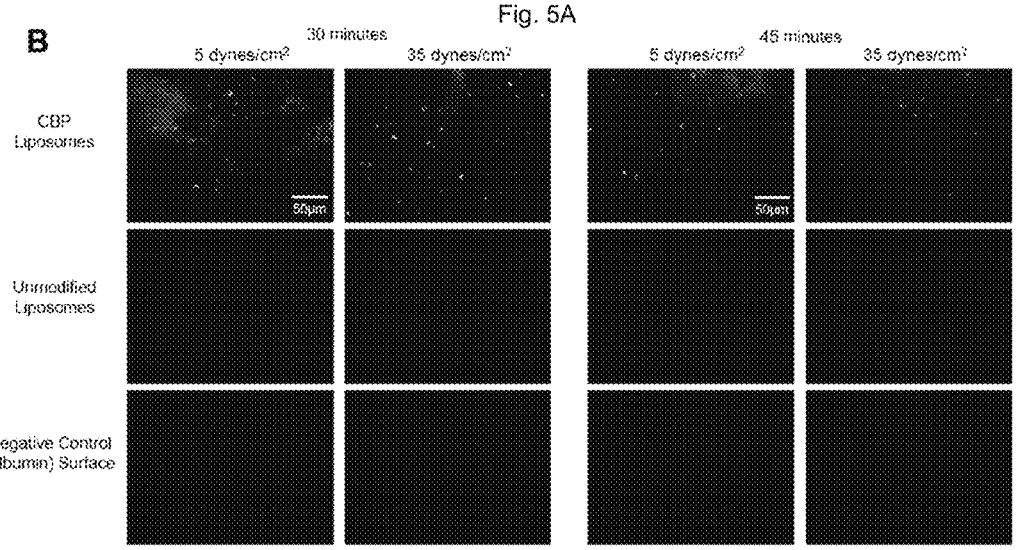
Fig. 5A
Fig. 5B

B

C

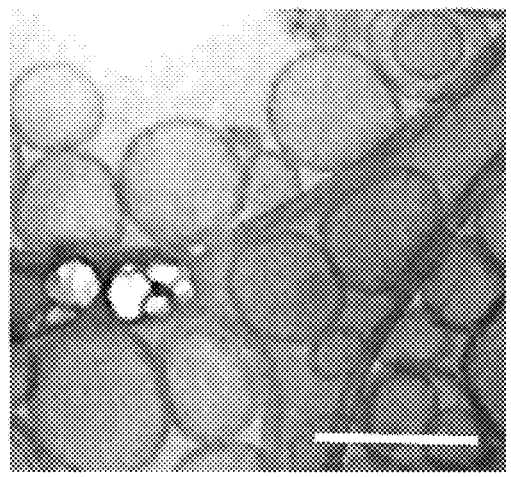
Fig. 13D
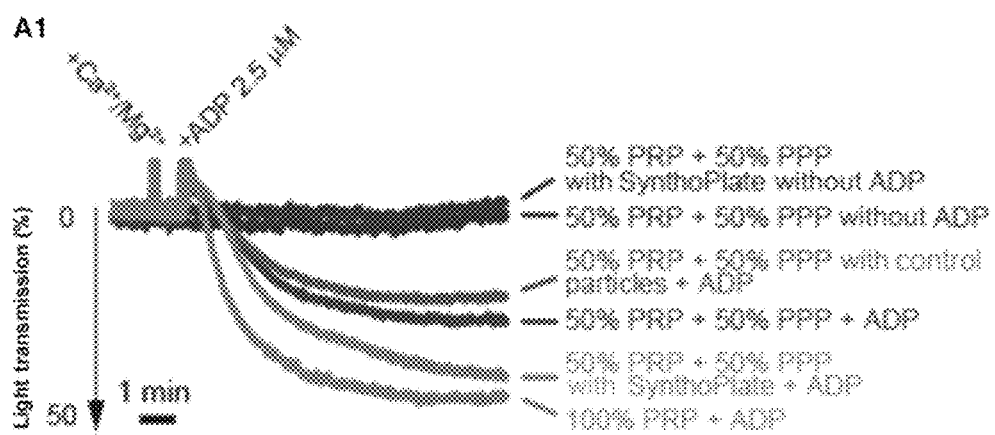
Fig. 14A1

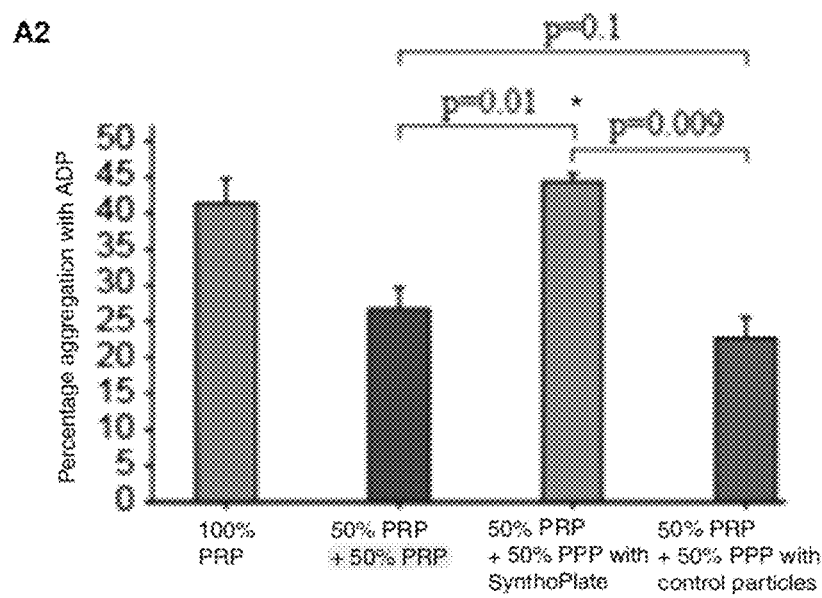
Fig. 14A2
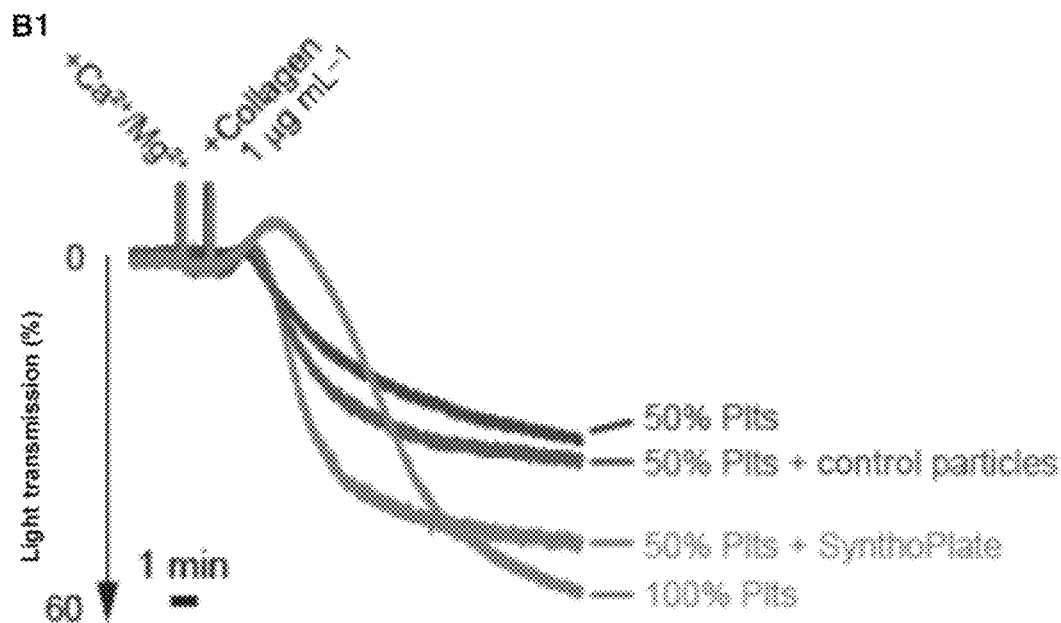
Fig. 14B1

Fig. 14B2

| GROUPS | Lag time (min) | Time to peak (min) | Maximum thrombin activity slope/s |
|---|---|---|---|
| PPP | 20 ± 3.51 | 24.33 ± 1.86 | 21.67 ± 1.67 |
| PRP | 33.33 ± 1.20 | 46.33 ± 5.46 | 22.78 ± 2.42 |
| PPP + SynthoPlate | 27.67 ± 3.84 | 31 ± 3.46 | 22.22 ± 1.47 |
| PRP + SynthoPlate | 34.33 ± 1.86 | 40.67 ± 1.86 | 25.56 ± 7.22 |
| PPP + tissue factor | 1 ± 0 | 3.33 ± 0.88 | 77.22 ± 7.47 |
| PRP + tissue factor | 1 ± 0 | 3.67 ± 1.20 | 92.22 ± 2.94 |
| PRP + SynthoPlate + Tissue Factor | 1 ± 0 | 5.33 ± 1.76 | 88.89 ± 13.14 |
| PRP + ADP + Tissue Factor | 1.33 ± 0.33 | 3.33 ± 0.67 | 117.22 ± 11.40 |
| PRP + ADP + SynthoPlate + Tissue Factor | 1.33 ± 0.33 | 4 ± 0.57 | 124.44 ± 9.15 |

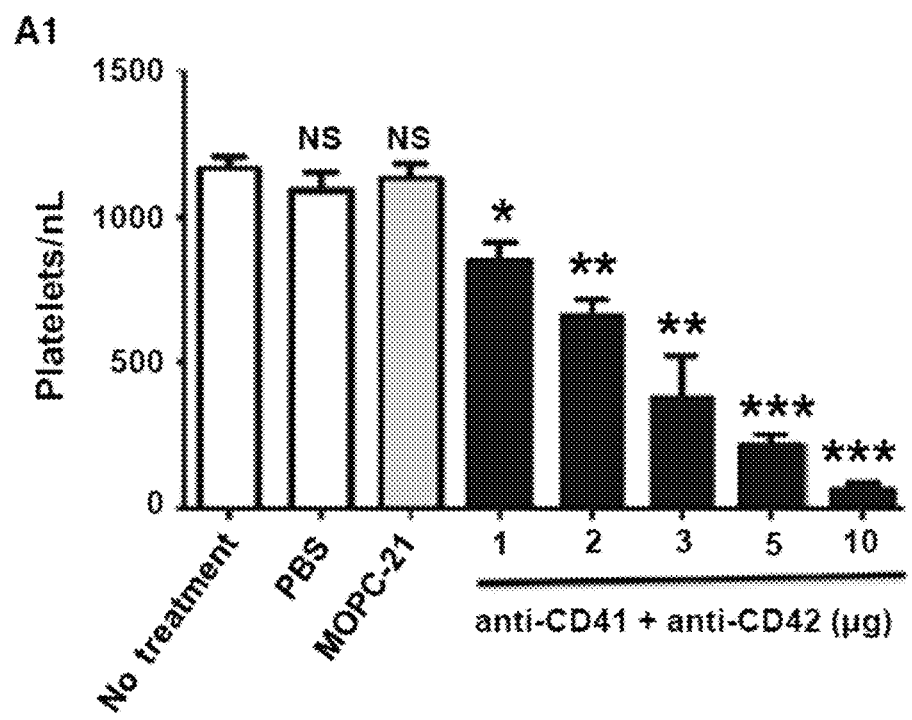
Fig. 16A1
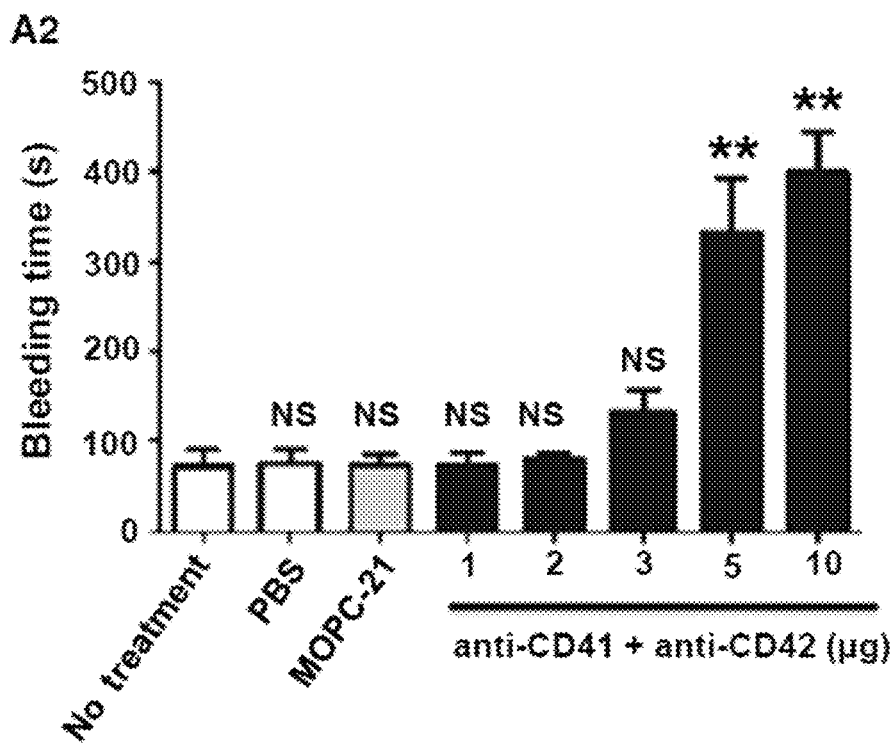
Fig. 16A2

C

D

SYNTHETIC PLATELETS

RELATED APPLICATION

This application is a Continuation-in-Part of U.S. patent application Ser. No. 14/826,387, filed Aug. 14, 2015, now U.S. Pat. No. 9,686,383, which is a Continuation of U.S. patent application Ser. No. 14/111,650, filed Dec. 18, 2013, which is a National Phase filing of PCT/US2012/033444, filed Apr. 13, 2012, which claims priority from U.S. Provisional Application No. 61/475,039, filed Apr. 13, 2011, the subject matter of which are incorporated herein by reference in their entirety.

GOVERNMENT FUNDING

This invention was made with government support under Grant No. F31-DE019998, R01HL121212, R01HL089796 awarded by The National Institutes of Health. R35GM119526, awarded by the National Institute of General Science. The United States government has certain rights in the invention.

TECHNICAL FIELD

This application relates to compositions and methods of reducing or diminishing bleeding and blood loss and particularly relates to synthetic platelets and to their use in diminishing bleeding and blood loss.

BACKGROUND

Traumatic injury is the leading cause of death for individuals between the ages of 5 and 44, and blood loss is the major factor in both civilian and battlefield traumas. Following injury, hemostasis is established through a series of coagulatory events including platelet activation. However, with severe injuries, these processes are insufficient and result in uncontrolled bleeding. Methods to staunch bleeding have included pressure dressings and absorbent materials, but these treatments are limited to compressible and exposed wounds. Alternatives have included allogeneic platelet transfusions, clotting factors, and platelet substitutes, but efficacy, immunogenicity, and thrombosis have stalled their application. Immediate intervention is one of the most effective means of minimizing mortality associated with severe trauma.

Administration of allogenic platelets are a logical means to halt bleeding; however, platelets have a short shelf life, and administration of allogenic platelets can cause graft versus host disease, alloimmunization, and transfusion-associated lung injuries. Recombinant factors including Factor VIIa can augment hemostasis, but immunogenic and thromboembolic complications are unavoidable risks. Nonetheless, administration of recombinant factors has become the standard of care in a number of trauma and surgical situations where bleeding cannot otherwise be controlled. Non-platelet alternatives including red blood cells modified with the Arg-Gly-Asp (RGD) sequence, fibrinogen-coated microcapsules based on albumin, and liposomal systems have been studied as coagulants, but toxicity, thrombosis, and limited efficacy have stalled many of these products.

SUMMARY

This application relates to a synthetic platelet that includes a biocompatible flexible nanoparticle. The nanoparticle includes an outer surface and a plurality of peptides conjugated to the surface. The peptides include a plurality of von Willebrand factor-binding peptides (VBPs), collagen-binding peptides (CBPs) and active platelet GPM-IIIa-binding peptides (GBPs). The VBPs, CBPs, and GBPs can be spatially or topographically arranged on the flexible nanoparticle surface such that the VBPs, CBPs, and GBPs do not spatially mask each other and the synthetic platelet is able to adhere to a vascular surface, vascular disease site, and/or vascular injury site with exposed vWF and collagen and promote arrest and aggregation of active platelets onto sites of the synthetic platelet adhesion.

In some embodiments, the flexible nanoparticle shape, size and elastic modulus facilitates upon administration to a vasculature of a subject margination to a vascular wall and their bio-interactions. For example, the flexible nanoparticle can have an about 2 to about 5 μm diameter discoidal shape and an about 10 to about 50 kPa mechanical elastic modulus.

In some embodiments, the VBPs can include a peptide having SEQ ID NO: 1, the CBPs can include a peptide having SEQ ID NO: 2, and the GBPs can include a peptide having SEQ ID NO: 3.

In other embodiments, the ratio of VPBs to CPBs provided on the nanoparticle surface is about 70:30 to about 30:70. In still other embodiments, the ratio of VPB:CPB:GBP is about 1:1:2 to 1:2:1 to 2:1:1.

In some embodiments, the nanoparticle can include a liposome. In other embodiments, the nanoparticle can include an outer shell that comprises alternating layers of albumin and a polyallyamine.

In some embodiments, the synthetic platelets can be used in a method of promoting aggregation of activated platelets on a site with exposed vWF and collagen. In other embodiments, the synthetic platelets can be used in a method of method of diminishing bleeding in a subject. In still other embodiments, the synthetic platelets can be used in a method of treating a vascular injury.

In some embodiments, the subject can have or be at increased risk of thrombocytopenia. The thrombocytopenia can be caused by or result from dehydration, leukemia, myelodysplastic syndrome, aplastic anemia, liver failure, sepsis, leptospirosis, congenital amegakaryocytic thrombocytopenia, thrombocytopenia absent radius syndrome, fanconi anemia, Bernard-Soulier syndrome, May-Hegglin anomaly, grey platelet syndrome, Alport syndrome, Wiskott-Aldrich syndrome, idiopathic thrombocytopenic purpura, thrombotic thrombocytopenia purpura, hemolytic-uremic syndrome, disseminated intravascular coagulation, paroxysmal nocturnal hemoglobinuria, antiphospholipid syndrome, systemic lupus erythematosus, post-transfusion purpura, neonatal alloimmune thrombocytopenia, hypersplenism, dengue fever, Gaucher's disease, zika virus, medication-induced thrombocytopenia, niacin toxicity, Lyme disease, and thrombocytapheresis.

Figure 1:
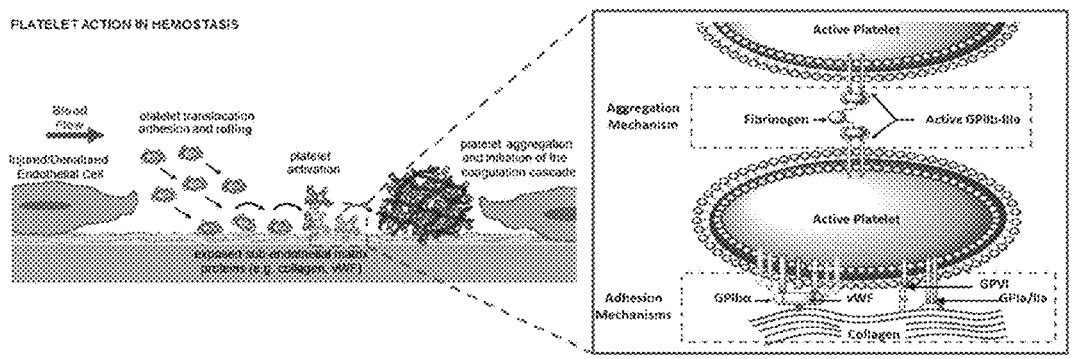
FIG. 1 is a schematic representation of molecular mechanisms of adhesion and aggregation of blood platelets in primary hemostasis. The adhesion is mediated by binding of the extracellular domain of GPIbα of the platelet surface receptor GPIb/IX/V to vWF and binding of the platelet surface receptors GPIa/IIa and GPVI to collagen.

FIG. 4 illustrates representative fluorescent micrographs from PPFC experiments where VBP-modified liposomes were allowed to flow with soluble vWF over collagen surface versus albumin surface under high shear (55 dynes/$cm^2$). Soluble vWF cannot adhere and multimerize on albumin surface, but can adhere and multimerize on collagen surface; consequently with time (5 min to 30 min of flow) the soluble vWF formed larger multimerized areas on collagen surface, allowing higher extent of adhesion of green fluorescent VBP-modified liposomes. Adhesion of VBP modified liposomes on the albumin surface was minimum since there was no vWF multimerization on albumin.

FIGS. 5(A-C) illustrate representative results from PPFC studies using CBP-decorated liposomal constructs allowed to flow over collagen-coated surface versus albumin surface. (A) schematic of experimental set-up; (B) the ligand-modified liposomes showed minimal adhesion or retention on albumin surface and the unmodified liposomes showed minimal adhesion or retention on collagen surface, whereas the CBP-modified liposomes showed significant adhesion and retention on collagen surface under flow; (C) quantitative analysis of the adhesion (at 30 min) and retention (at 45 min) data using surface-averaged fluorescence intensity shows that the CBP modified liposomes undergo enhanced adhesion and retention on the collagen surface in a shear independent fashion.

FIGS. 6(A-B) illustrate representative results from PPFC studies using heteromultivalent liposomal constructs surface-modified with both vWF-binding (rGPIbα or VBP) and collagen-binding (CBP) ligand motifs allowed to flow over vWF/collagen mixed (50:50) surface versus albumin surface. (A) The heteromultivalent ligand-modified liposomes showed minimal adhesion or retention on albumin surface and the unmodified liposomes showed minimal adhesion or retention on the vWF/collagen mixed surface, whereas, the liposomes modified simultaneously with both vWF binding and collagen-binding ligand motifs showed significant adhesion and retention on the vWF/collagen mixed surface; (B) quantitative analysis of the adhesion (at 30 min) and retention (at 45 min) data using surface-averaged fluorescence intensity shows that the liposomes surface modified simultaneously with rGPIbα and CBP (red bars) do not undergo statistically different adhesion and retention on the vWF/collagen surface compared to liposomes surface-modified with rGPIbα alone, whereas, liposomes modified with VBP and CBP (indigo bars) undergo significantly enhanced adhesion and retention on the vWF/collagen surface compared to liposomes surface-modified with VBP alone and CBP alone, under increasing shear stress.

FIG. 7 is a schematic of methods to fabricate functionally integrated liposomes bearing VBP and CBP peptides for platelet-mimetic vWF and collagen adhesion under flow and cRGD peptides to promote arrest and aggregation of active platelets via interaction with integrin GPIIb/IIIa.

FIG. 8 is a schematic representation and representative fluorescent images from studies of platelet aggregation in absence or presence of ADP on unmodified versus cRGD-modified biotinylated liposomes pre-adhered as monolayer on avidin-coated coverslips. Only cRGD-modified liposomes show enhanced arrest and aggregation of platelets (red fluorescence) onto them in presence of ADP-induced activation. For imaging, platelets were stained with P-selectin specific AlexaFluor 647-anti-CD62P antibody and imaged using a Zeiss Axio Observer.D1 inverted fluorescence microscope fitted with a photometrics chilled CCD camera and a 63× objective.

FIG. 9 is a schematic of the parallel plate flow chamber (PPFC) preparation with adjacent albumin-coated (negative control) and mixed (vWF/collagen)-coated areas and anticipated interaction of peptide (VBP and CBP)-modified liposomes with the surfaces under flow.

FIG. 10 illustrates quantitative analysis of platelet aggregation on avidin-coated coverslip-attached cRGD-modified versus unmodified biotinylated liposomal constructs, in absence or presence of ADP. cRGD-modified liposomes promote significant aggregation of ADP-activated platelets compared to the other conditions.

FIG. 11 illustrates experimental conditions and resultant representative fluorescence images of unmodified and various peptide-modified liposomal constructs with low concentrations of activated platelets under flow on albumin-coated and vWF/collagen-coated surface in the PPFC. Green fluorescence (from DSPE-PEG-Fluorescein) represents liposomal constructs adhered onto vWF/collagen, red fluorescence (from AlexaFluor647-anti-CD62P) represents activated platelets aggregated in the same field of view as the liposome adhesion images, and the yellow overlay represents co-localization of the green and red fluorescence signifying adhered liposome promoted aggregation of active platelets. Only images at the 45 minute time point for shear stress value of 35 dynes/$cm^2$ are shown here for convenience.

FIGS. 12(A-C) illustrate a quantitative analysis of the fluorescence data of liposome adhesion (A) (green fluorescence intensity quantification), (B) platelet aggregation (red fluorescence intensity quantification), and (C) co-localization of green and red fluorescence, from PPFC experiments with unmodified and various peptide-modified liposomal constructs with low concentrations of activated platelets under flow on vWF-collagen surface. The data is shown for wall shear stress values of 5-55 dynes/$cm^2$ at the 45 minute time point. The results demonstrate that the functionally integrated liposomes (surface-modified simultaneously by VBP, CBP and RGD) have significantly enhanced capacity to adhere to the vWF/collagen surface under flow at the various shear stress values and promote significant arrest and aggregation of active platelets from flow onto themselves.

FIGS. 13(A-D) illustrate manufacture and characterization of SynthoPlate constructs. (A) Schematic representation of SynthoPlate manufacture, in which DSPC, DSPE-PEG peptides (DSPE-PEG-VBP, DSPE-PEG-CBP, and DSPE-PEG-FMP), cholesterol and lipid-Rhodamine B (RhB) were selfassembled at controlled concentrations with a reverse-phase evaporation and extrusion technique to form heteromultivalently peptide-decorated vesicles. (B-D) Dynamic light scattering (B), scanning electron microscopy (C) and cryo-transmission electron microscopy (D) characterization of the SynthoPlate vesicles shows a narrow size distribution, with an average diameter of ~150 nm. Scale bars in (B) and (C): 200 nm. CBP, collagen-binding peptide; FMP, fibrinogen-mimetic peptide; VBP, von Willebrand factor-binding peptide.

FIGS. 14(A(1-2)-B(1-2) illustrate ex vivo aggregometry studies for SynthoPlate with mouse platelets. Representative aggregometry traces (A1, B1) and corresponding percentage platelet aggregation histograms (A2, B2) of SynthoPlate versus control (unmodified) particles for platelet-rich plasma (PRP) with ADP as agonist and a washed platelet suspension (Plts) with collagen as agonist. SynthoPlate itself does not activate and aggregate resting platelets (the brown trace is similar to the indigo trace in [A1]). Addition of platelet agonist (ADP in [A1] and collagen in [B1]) to 100% PRP or 100% Plts significantly enhances aggregation (green traces in [A1] and [B1]), but this aggregation is significantly decreased if the PRP is 50% diluted with platelet-poor plasma (PPP) or Plts is 50% diluted with phosphate-buffered saline (PBS) (purple traces in [A1] and [B1]). Addition of control (unmodified) particles in the diluting volume of PPP or Plts does not improve this aggregation (red traces in [A1] and [B1]), but addition of SynthoPlate to the diluting volume of PPP or Plts significantly improves aggregation (cyan traces in [A1] and [B1]). Corresponding histograms (A2, B2) clearly show the ability of SynthoPlate to improve percentage aggregation of ADP-activated platelets in 50% diluted PRP and of collagen-activated platelets in 50% diluted Plts.

FIGS. 15(A-D) illustrate Effect of SynthoPlate on secondary hemostasis (thrombin generation and fibrin deposition). (A) A table showing the results from thrombin generation assays indicates that SynthoPlate itself does not have the ability to rapidly activate coagulation factors in plasma to generate thrombin, as adding only SynthoPlate to recalcified platelet-rich plasma (PRP) or platelet-poor plasma (PPP) without tissue factor (TF) or platelet agonist (e.g., ADP) has no accelerating effect on thrombin generation, and the thrombin generation is enhanced only upon TF and/or ADP addition to PRP or PPP, with SynthoPlate slightly enhancing this effect (possibly by recruitment and clustering of active platelets in suspension). (B, C) Representative fluorescence images at the 15-min time-point (B) and (C) surface-averaged fluorescence intensity values at the 5-min and 15-min time-points of fibrin(ogen) generation/deposition on 'von Willebrand factor (VWF)+collagen' surface (C) in the parallelplate flow chamber experiments show that resting platelets (without ADP) in 50% PRP (diluted with PPP) generate/deposit only minimal levels of fibrin(ogen) as they interact with the 'VWF+collagen' surface, and that this generation/deposition increases if platelet agonist is introduced into the flow (i.e., with ADP). Introducing SynthoPlate vesicles into the flow along with ADP-activated platelets in 50% PRP significantly enhances fibrin(ogen) generation/deposition during the 15-min flow period, as compared with flow with 'adhesion-only' particles (control) and even as compared with flow of 100% PRP (with ADP) without SynthoPlate. (D) D-dimer analysis of the generated/deposited clots on the 'VWF+collagen' surface confirms that the clots resulting from enhanced clot formation in the SynthoPlate-added group are indeed rich in fibrin, and that the process does not just involve fibrinogen binding to recruited active platelets.

FIGS. 16(A(A1-A2)-B) illustrate the development of thrombocytopenia model in mouse and evaluation of SynthoPlate capability in correcting tail transection bleeding time in thrombocytopenic mouse. (A) Experimental design for antibody-induced thrombocytopenia in mice and subsequent tail-bleeding studies, in which (A1) dose-dependent depletion of platelets resulted in (A2) a corresponding increase in bleeding time after tail transection (10 μg of antibody cocktail dose resulted in ~90% platelet depletion and a corresponding four-fold to five-fold increase in bleeding time as compared with normal mice). (B) Severely thrombocytopenic (TCP) mice injected with phosphate-buffered saline (PBS) or control (unmodified) particles at various doses show no improvement (reduction) in bleeding time, but TCP mice injected with SynthoPlate vesicles show a dose-dependent significant improvement in bleeding time, with the highest dose (1000 $nL^{-1}$, equivalent to the normal murine platelet count) reducing the bleeding time to ~150 s (close to the bleeding time of ~100 s for normal mice, shown for comparison); $*P \leq 0.05$, $P \leq 0.01$, and $*P \leq 0.001$. NS, not significant.

FIGS. 17(A-D) illustrate characterization of SynthoPlate-mediated hemostatic clot in transected tail of thrombocytopenic mouse. (A, B) Representative immunofluorescence microscopy images of tail tissue cryosections (transverse section) proximal to the hemostasized injury site, showing vascular endothelium (blue, CD31), particles (red, Rhodamine B), platelets (green, CD41), and corresponding overlays, indicate that (A) tail tissues from SynthoPlate-injected mice have significant colocalization of endothelium, particles, and platelet fluorescence, whereas (B) those from control particle-injected mice show minimal colocalization. Representative scale bar: 25 μm. (C) The percentage of blood vessels showing significant colocalization of particle fluorescence (red) and platelet fluorescence (green) was significantly higher in SynthoPlate-injected thrombocytopenic (TCP) mice than in control (unmodified) particle-injected mice ($***P \leq 0.001$). (D) Immunoblot analysis of injured tail tissue from SynthoPlate-treated TCP mice shows a significantly higher amount of high molecular weight fibrin than in tail tissue from control particle-treated TCP mice.

FIGS. 18(A-D) illustrate evaluation of systemic procoagulant risk and biodistribution of SynthoPlate in mice. (A, B) Prothrombin fragment 1+2 ELISA assay (A) and (B) Stago D-dimer assay in mice injected with SynthoPlate indicate that SynthoPlate vesicles do not trigger spontaneous formation of thrombin and fibrin in plasma (minimal systemic procoagulant risk). (C, D) Representative fluorescent images (blue, 40,6-diamidino-2-phenylindole-stained nuclei, red, Rhodamine B-labeled particles) of harvested tissue cryosections (C) and histogram showing systemic localization of SynthoPlate vesicles (D) in thrombocytopenic mice at the 2-h circulation time-point indicate that ~15% of the injected dose is cleared during the 2-h period, with the liver and spleen being the principal organs of vesicle clearance, with much reduced clearance in kidney, heart, and lungs. LPS, lipopolysaccharide.

DETAILED DESCRIPTION

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The term "about" will be understood by persons of ordinary skill in the art and will vary to some extent on the context in which it is used.

The term "antibody," as used herein, refers to an immunoglobulin molecule, which is able to specifically bind to a specific epitope on an antigen. Antibodies can be intact immunoglobulin's derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

A "conservative substitution" is the substitution of an amino acid with another amino acid with similar physical and chemical properties. In contrast, a "nonconservative substitution" is the substitution of an amino acid with another amino acid with dissimilar physical and chemical properties.

As used herein, "homology" is used synonymously with "identity."

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 5'-ATTGCC-3' and 5'-TATGGC-3' share 50% homology.

The terms "diminishing," "reducing," or "preventing," "inhibiting," and variations of these terms, as used herein include any measurable decrease, including complete or substantially complete inhibition.

A "recombinant polypeptide" is one, which is produced upon expression of a recombinant polynucleotide.

"Mutants," "derivatives," and "variants" of a polypeptide (or of the DNA encoding the same) are polypeptides which may be modified or altered in one or more amino acids (or in one or more nucleotides) such that the peptide (or the nucleic acid) is not identical to the wild-type sequence, but has homology to the wild type polypeptide (or the nucleic acid).

A "mutation" of a polypeptide (or of the DNA encoding the same) is a modification or alteration of one or more amino acids (or in one or more nucleotides) such that the peptide (or nucleic acid) is not identical to the sequences recited herein, but has homology to the wild type polypeptide (or the nucleic acid).

"Nanoparticle" as used herein is meant to include particles, spheres, capsules, and other structures having a length or diameter of about 10 nm to about 10 µm. For the purposes of this application, the terms "nanosphere", "nanoparticle", "nanocapsule", "microsphere", "microparticle", and "microcapsule" are used interchangeably.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

A "portion" of a polypeptide means at least about three sequential amino acid residues of the polypeptide. It is understood that a portion of a polypeptide may include every amino acid residue of the polypeptide.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual and partial numbers within that range, for example, 1, 2, 3, 4, 5, 5.5 and 6. This applies regardless of the breadth of the range.

This application relates to synthetic platelets and to their use in diminishing bleeding and blood loss as well as to compositions and methods useful in the delivery of therapeutic agents to the vasculature. The synthetic platelets described herein, unlike previously described synthetic platelets, integrate platelet-mimetic adhesion- and aggregation-promoting functionalities on a single flexible nanoparticle. It was found that the platelet-mimetic adhesion- and aggregation-promoting functionalities can be achieved by including on, conjugating to, or decorating a flexible nanoparticle with a plurality of three peptides, i.e., a von Willebrand factor-binding peptide (VBP), a collagen-binding peptide (CBP) and an active platelet GPIIb-IIIa-binding peptide (GBP). It was initially found that liposomes bearing VBP and CBP motifs undergo platelet-mimetic adhesion under flow on vWF and collagen-coated surfaces in vitro at low-to-high shear in parallel plate flow chamber (PPFC) experiments and that GBP-modified liposomes pre-adhered to a surface can enhance the aggregation of ADP-activated platelets onto them, even at a low platelet concentrations. Subsequently, it was found that liposomes bearing all three peptides (VBP, CBP and GBP), when introduced in PPFC flow along with low concentration of ADP-activated platelets over a vWF/collagen mixed coated surface, are able to adhere to the surface under high shear and promote arrest and aggregation of active platelets onto sites of liposome adhesion.

It is therefore an aspect of the application that administration, such as for example intravenous administration, of the synthetic platelets described herein to a subject with a vascular injury can diminish the bleeding time in the subject. It is a further aspect of the application that the synthetic platelets provide a nanostructure that binds with a vascular injury site as well as activated platelets and enhances their rate of aggregation to aid in stopping bleeding and particularly hemorrhage from traumatic injury, medical bleeding, and non-compressible hemorrhage.

In some embodiments, the subject can have or be at increased risk of thrombocytopenia. The thrombocytopenia can be caused by or result from dehydration, leukemia, myelodysplastic syndrome, aplastic anemia, liver failure, sepsis, leptospirosis, congenital amegakaryocytic thrombocytopenia, thrombocytopenia absent radius syndrome, fanconi anemia, Bernard-Soulier syndrome, May-Hegglin anomaly, grey platelet syndrome, Alport syndrome, Wiskott-Aldrich syndrome, idiopathic thrombocytopenic purpura, thrombotic thrombocytopenia purpura, hemolytic-uremic syndrome, disseminated intravascular coagulation, paroxysmal nocturnal hemoglobinuria, antiphospholipid syndrome, systemic lupus erythematosus, post-transfusion purpura, neonatal alloimmune thrombocytopenia, hypersplenism, dengue fever, Gaucher's disease, zika virus, medication-induced thrombocytopenia, niacin toxicity, Lyme disease, and thrombocytapheresis.

In other embodiments, the synthetic platelets described herein can be used to treat a bleeding disorder. In one embodiment, the bleeding disorder is hemophilia. In a further embodiment, the hemophilia is hemophilia A. In yet another embodiment the hemophilia is hemophilia B. In one embodiment, the hemophilia is hemophilia A. In another embodiment, the hemophilia is acquired hemophilia A with inhibitory auto antibodies to FVIII. In one embodiment, the hemophilia is congenital hemophilia B with inhibitors. In another embodiment, the hemophilia is acquired hemophilia B with inhibitory auto antibodies to FIX.

In other embodiments, the bleeding disorder is a non-hemophilia bleeding disorder. In one embodiment, the bleeding disorder is blood loss from trauma. In another embodiment, the bleeding disorder is FVII deficiency. In one embodiment, the bleeding disorder is FV deficiency. In another embodiment, the bleeding disorder is FX deficiency. In one embodiment, the bleeding disorder is FXI deficiency. In one embodiment, the bleeding disorder is FXIII deficiency. In one embodiment, the bleeding disorder is fibrinogen deficiency. In one embodiment, the bleeding disorder is prothrombin deficiency. In another embodiment, the bleeding disorder is dilutional coagulopathy. In a further embodiment, the bleeding disorder is thrombocytopenia. In yet another embodiment, the bleeding disorder is blood loss from high-risk surgeries. In another embodiment, the bleeding disorder is intracerebral hemorrhage. In one embodiment, the bleeding disorder is von Willebrand disease. In a further embodiment, the bleeding disorder is von Willebrand disease with inhibitors to von Willebrand factor.

In other embodiments, the bleeding disorder is a congenital platelet function defect, including, but not limited to, platelet storage pool disorder, Glanzmann's thrombasthenia, or Bernard-Soulier syndrome. In one embodiment, the bleeding disorder is an acquired platelet function defect. In one embodiment, the bleeding disorder is a congenital deficiency of Factor II, Factor V, Factor VII, Factor X, or Factor XI. In one embodiment, the bleeding disorder is neonatal and pediatric coagulopathies. In one embodiment, the bleeding disorder is a platelet function disorder. In another embodiment, the bleeding disorder is heparin-induced thrombocytopenia. In one embodiment, the bleeding disorder is disseminated intravascular coagulation.

In other embodiments, the non-hemophilia bleeding disorder is blood loss from trauma. In another embodiment, the non-hemophilia bleeding disorder is FVII deficiency. In one embodiment, the non-hemophilia bleeding disorder is FV deficiency. In another embodiment, the non-hemophilia bleeding disorder is FX deficiency. In one embodiment, the non-hemophilia bleeding disorder is FXI deficiency. In one embodiment, the non-hemophilia bleeding disorder is FXIII deficiency. In one embodiment, the non-hemophilia bleeding disorder is fibrinogen deficiency. In one embodiment, the non-hemophilia bleeding disorder is prothrombin deficiency. In another embodiment, the non-hemophilia bleeding disorder is dilutional coagulopathy. In a further embodiment, the non-hemophilia bleeding disorder is thrombocytopenia. In yet another embodiment, the non-hemophilia bleeding disorder is blood loss from high-risk surgeries. In another embodiment, the non-hemophilia bleeding disorder is intracerebral hemorrhage. In one embodiment, the non-hemophilia bleeding disorder is von Willebrand disease. In a further embodiment, the non-hemophilia bleeding disorder is von Willebrand disease with inhibitors to von Willebrand factor.

In one embodiment, the non-hemophilia bleeding disorder is a congenital platelet function defect, including, but not limited to, platelet storage pool disorder, Glanzmann's thrombasthenia, or Bernard-Soulier syndrome. In one embodiment, the non-hemophilia bleeding disorder is an acquired platelet function defect. In one embodiment, the non-hemophilia bleeding disorder is a congenital deficiency of Factor II, Factor V, Factor VII, Factor X, or Factor XI. In one embodiment, the non-hemophilia bleeding disorder is neonatal and pediatric coagulopathies. In one embodiment, the non-hemophilia bleeding disorder is a platelet function disorder. In another embodiment, the non-hemophilia bleeding disorder is heparin-induced thrombocytopenia. In one embodiment, the non-hemophilia bleeding disorder is disseminated intravascular coagulation. In other embodiments, the non-hemophilia bleeding disorder is any disorder known to one of skill in the art.

In some embodiments, the synthetic platelets described herein can include a biocompatible, biodegradable, flexible nanoparticle core and a plurality of VBPs, CBPs, and GBPs bound to, conjugated to, and/or decorated on the a surface defined by the flexible nanoparticle core. The VBPs, CBPs, and GBPs can be spatially or topographically arranged on the flexible nanoparticle surface such that the VBPs, CBPs, and GBPs do not spatially mask each other and are able to adhere to a vascular surface, vascular disease site, and/or vascular injury site with exposed vWF and collagen and promote arrest and aggregation of active platelets onto sites of nanoparticle adhesion.

The biocompatible, biodegradable, flexible nanoparticles can be made from any biocompatible, biodegradable material that can form a flexible nanoparticle to which the peptides described herein can be attached, conjugated, and/or decorated. In some embodiments, the biocompatible, biodegradable flexible nanoparticles can include a liposome, a hydrogel, micelle, and/or polymer, which can include and/or be surface modified or engineered with the VBPs, CBPs, and GBPs.

The liposome or hydrogel can include a lipid and/or any naturally-occurring, synthetic or semi-synthetic (i.e., modified natural) moiety that is generally amphipathic (i.e., including a hydrophilic component and a hydrophobic component). Examples of lipids can include fatty acids, neutral fats, phospholipids, oils, glycolipids, surfactants, aliphatic alcohols, waxes, terpenes and steroids. Semi-synthetic or modified natural lipids can include natural lipids that have been chemically modified in some fashion. The at least one lipid can be neutrally-charged, negatively-charged (i.e., anionic), or positively-charged (i.e., cationic). Examples of anionic lipids can include phosphatidic acid, phosphatidyl glycerol, and fatty acid esters thereof, amides of phosphatidyl ethanolamine, such as anandamides and methanandamides, phosphatidyl serine, phosphatidyl inositol and fatty acid esters thereof, cardiolipin, phosphatidyl ethylene glycol, acidic lysolipids, sulfolipids and sulfatides, free fatty acids, both saturated and unsaturated, and negatively-charged derivatives thereof. Examples of cationic lipids can include N-[1-(2,3-dioleoyloxy)propyl]-N,N,N-trimethylammonium chloride and common natural lipids derivatized to contain one or more basic functional groups.

Other examples of lipids, any one or combination of which may be used to form the nanoparticle, can include: phosphocholines, such as 1-alkyl-2-acetoyl-sn-glycero 3-phosphocholines, and 1-alkyl-2-hydroxy-sn-glycero 3-phosphocholines; phosphatidylcholine with both saturated and unsaturated lipids, including dioleoylphosphatidylcholine, dimyristoylphosphatidylcholine, dipentadecanoylphosphatidylcholine, dilauroylphosphatidylcholine, dipalmitoylphosphatidylcholine (DPPC), distearoylphosphatidylcholine (DSPC), and diarachidonylphosphatidylcholine (DAPC); phosphatidylethanolamines, such as dioleoylphosphatidylethanolamine, dipalmitoylphosphatidylethanolamine (DPPE), and distearoylphosphatidylethanolamine (DSPE); phosphatidylserine; phosphatidylglycerols, including distearoylphosphatidylglycerol (DSPG); phosphatidylinositol; sphingolipids, such as sphingomyelin; glycolipids, such as ganglioside GM1 and GM2; glucolipids; sulfatides; glycosphingolipids; phosphatidic acids, such as dipalmitoylphosphatidic acid (DPP A) and distearoylphosphatidic acid (DSPA); palmitic acid; stearic acid; arachidonic acid; oleic acid; lipids bearing polymers, such as chitin, hyaluronic acid, polyvinylpyrrolidone or polyethylene glycol (PEG); lipids bearing sulfonated mono-, di-, oligo- or polysaccharides; cholesterol, cholesterol sulfate, and cholesterol hemisuccinate; tocopherol hemisuccinate; lipids with ether and ester-linked fatty acids; polymerized lipids (a wide variety of which are well known in the art); diacetyl phosphate; dicetyl phosphate; stearylaamine; cardiolipin; phospholipids with short chain fatty acids of about 6 to about 8 carbons in length; synthetic phospholipids with asymmetric acyl chains, such as, for example, one acyl chain of about 6 carbons and another acyl chain of about 12 carbons; ceramides; non-ionic liposomes including niosomes, such as polyoxyalkylene (e.g., polyoxyethylene) fatty acid esters, polyoxyalkylene (e.g., polyoxyethylene) fatty alcohols, polyoxyalkylene (e.g., polyoxyethylene) fatty alcohol ethers, polyoxyalkylene (e.g., polyoxyethylene) sorbitan fatty acid esters (such as, for example, the class of compounds referred to as TWEEN (commercially available from ICI Americas, Inc., Wilmington, Del.), glycerol polyethylene glycol oxystearate, glycerol polyethylene glycol ricinoleate, alkyloxylated (e.g., ethoxylated) soybean sterols, alkyloxylated (e.g., ethoxylated) castor oil, polyoxyethylene-polyoxypropylene polymers, and polyoxyalkylene (e.g., polyoxyethylene) fatty acid stearates; sterol aliphatic acid esters including cholesterol sulfate, cholesterol butyrate, cholesterol isobutyrate, cholesterol palmitate, cholesterol stearate, lanosterol acetate, ergosterol palmitate, and phytosterol n-butyrate; sterol esters of sugar acids including cholesterol glucuronide, lanosterol glucuronide, 7-dehydrocholesterol glucuronide, ergosterol glucuronide, cholesterol gluconate, lanosterol gluconate, and ergosterol gluconate; esters of sugar acids and alcohols including lauryl glucuronide, stearoyl glucuronide, myristoyl glucuronide, lauryl gluconate, myristoyl gluconate, and stearoyl gluconate; esters of sugars and aliphatic acids including sucrose laurate, fructose laurate, sucrose palmitate, sucrose stearate, glucuronic acid, gluconic acid and polyuronic acid; saponins including sarsasapogenin, smilagenin, hederagenin, oleanolic acid, and digitoxigenin; glycerol dilaurate, glycerol trilaurate, glycerol dipalmitate, glycerol and glycerol esters including glycerol tripalmitate, glycerol distearate, glycerol tristearate, glycerol dimyristate, glycerol trimyristate; long chain alcohols including n-decyl alcohol, lauryl alcohol, myristyl alcohol, cetyl alcohol, and n-octadecyl alcohol; 6-(5-cholesten-3-yloxy)-1-thio- -D-galactopyranoside; digalactosyldiglyceride; 6-(5-cholesten-3-yloxy)hexyl-6-amino-6-deoxy-1-thio- -D-galactopyranoside; 6-(5-cholesten-3-yloxy)hexyl-6-amino-6-deoxyl-1-thio-a-D-mannopyranoside; 12-(((7'-diethylaminocoumarin-3-yl) carbonyl)methylamino)octadecanoic acid; N-[12-(((7'-diethylaminocoumarin-3-yl)carbonyl)methylamino) octadecanoyl]-2-aminopalmitic acid; cholesteryl(4'-trimethylammonio)butanoate; N-succinyldioleoylphosphatidylethanolamine; 1,2-dioleoyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine and palmitoylhomocysteine; and/or any combinations thereof.

Examples of biocompatible, biodegradable polymers that can be used to form the nanoparticles are poly(lactide)s, poly(glycolide)s, poly(lactide-co-glycolide)s, poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polyacetyls, polycyanoacrylates, polyetheresters, poly(dioxanone)s, poly(alkylene alkylate)s, copolymers of polyethylene glycol and poly(lactide)s or poly(lactide-co-glycolide)s, biodegradable polyurethanes, and blends and/or copolymers thereof.

Other examples of materials that may be used to form the nanoparticles can include chitosan, poly(ethylene oxide), poly(lactic acid), poly(acrylic acid), poly(vinyl alcohol), poly(urethane), poly(N-isopropyl acrylamide), poly(vinyl pyrrolidone) (PVP), poly(methacrylic acid), poly(p-styrene carboxylic acid), poly(p-styrenesulfonic acid), poly(vinylsulfonicacid), poly(ethyleneimine), poly(vinylamine), poly (anhydride), poly(L-lysine), poly(L-glutamic acid), poly (gamma-glutamic acid), poly(carprolactone), polylactide, poly(ethylene), poly(propylene), poly(glycolide), poly(lactide-co-glycolide), poly(amide), poly(hydroxylacid), poly (sulfone), poly(amine), poly(saccharide), poly(HEMA), poly(anhydride), gelatin, glycosaminoglycans (GAG), poly (hyaluronic acid), poly(sodium alginate), alginate, albumin, hyaluronan, agarose, polyhydroxybutyrate (PHB), copolymers thereof, and blends thereof.

The flexible nanoparticles can have a maximum length or diameter of about 100 nm to about 10 μm and a substantially spherical, discoidal, and/or ellipsoidal shape. The physical size and shape as well as mechanical properties of the nanoparticles can be engineered to mimic those of natural platelets that are important in hemostasis. In some embodiments, the flexible nanoparticles can have an about 2 to about 5 μm diameter discoidal shape and an about 10 to about 50 kPa mechanical elastic modulus that mimics the size, shape, and elastic modulus of platelets and facilitates upon administration to the vasculature of a subject their margination to the vascular wall and their bio-interactions.

In an embodiment of the application, oblate ellipsoid nanoparticles having a diameter of about 2 to about 5 μm and a mechanical modulus of about 10 to about 50 kPa can be prepared by initially forming a polymer template. The polymer template can then be used to build a protein/ polymer shell using a cross-linked layer-by-layer assembly. The polymer template can subsequently be removed using solvents to leave behind soft, flexible, proteinaceous discoid particles having a diameter about 2 to about 5 μm and a mechanical elastic modulus of about 10 to about 50 kPa. The particles can then be surface-modified with the VBPs, CBPs, and GBPs at a surface density effective to promote maximum particle adhesion to vWF and collagen exposed surfaces at low-to-high sheer stresses and promote aggregation of active platelets even at low (less about 50,000 μl) platelet concentrations.

By way of example, poly-1-lactide-co-glycolide (PLGA) spherical particles having a diameter of about 2 to about 3 μm can be embedded into polyvinyl alcohol (PVA) film (e.g., about 5% w/v in water) containing 2% (v/v) glycerol as a plasticizer and biaxially stretched to twice the original length and width in an oven at about 65 C. The film can be removed from the stretcher and the PVA dissolved in 15% isopropanol followed by thorough washing with isopropanol to ensure complete removal of PVA. This results in the recovery of the oblate PLGA nanoparticles that can be resuspended in distilled water or PBS. These template particles can then be coated with protein and polyelectrolyte layers using a layer-by-layer (LBL) technique. For this, protein serum albumin (SA, e.g., human serum albumin or mouse serum albumin) and the polyelectrolyte polyallylamine hydrochloride (PAH) can be used at a 2 mg/ml concentration for adsorption. At the pH employed, albumin is negatively charged and PAH is cationic, alternate layers of SA and PAH can be formed on the PLGA template particles via electrostatic interactions. Multiple alternating layers (e.g., at least seven layers) can be formed on the oblate template and cross-linked with gluteraldehyde intermittently to enhance stability. The particles can then be exposed to a solvent mixture (e.g., 2:1 tetrahydrofuran:isopropanol) to dissolve the PLGA core, leaving behind the LBL deposited soft SA/PAH flexible discoid shell. The outermost layer can include albumin so that PEGylated peptides describe herein can be readily attached.

In some embodiments, the VBP peptide for vWF binding can include a recombinant GPIbα fragment (rGPIbα) containing the vWF binding sites (residues 1 to 302) or a short chain vWF-binding peptide. The GPIbα fragment can be expressed in CHO cells and isolated, adapting methods described. The short vWF-binding peptide can include the amino acid sequence of TRYLRIHPQSWVHQI (SEQ ID NO: 1). A peptide having an amino acid sequence of SEQ ID NO: 1 can be synthesized using fluorenylmethyloxycarbonyl chloride (FMoc)-based solid phase chemistry on Knorr resin, and characterized using mass spectroscopy. Each vWF molecule has only one binding region for this peptide, and hence vascular injury sites presenting multiple vWF binding sites for multiple copies of this peptide decorated on the nanoparticle surface, provide a mechanism for enhanced adhesion of the nanoparticles with increasing shear.

In some embodiments, the CBP can include a peptide that comprises a short seven-repeat of the tripeptide GPO (i.e., [GPO]$_7$, SEQ ID NO: 2) with a helicogenic affinity to fibrillar collagen. The GPO trimer is based on amino acid repeats found in the native collagen structure. It has been reported that the activation of platelets usually caused by interaction with collagen through GPVI and GPIa/IIa, can also potentially occur when platelets interact with collagen-derived peptides. This can be a potential problem regarding decorating synthetic particle surfaces with collagen-derived peptides for binding of collagen, because in vivo the constructs can potentially interact with quiescent blood platelets and systemically activate them, posing thromboembolic risks. However, interaction of platelet receptors with collagen and the subsequent platelet activation mechanisms are dependent upon receptor clustering induced by multimeric long chain triple-helical fibrillar collagen and not by short collagen-mimetic peptide repeats. In fact, it has been shown that GPO-trimer repeats as high as a 30-mer (10 repeats) only partially interact with platelet GPIa/IIa and GPVI integrins and are incapable of activating platelets; yet they can effectively bind to fibrillar collagen via helicogenic interaction. Hence, this small CBP can promote adhesion to fibrillar collagen, but cannot activate quiescent platelets due to absence of long triple-helical conformation. The CBP like the VBP can also be synthesized using FMoc-based solid phase chemistry on Knorr resin, and characterized using mass spectroscopy.

In some embodiments, the GBP can include an RGD amino acid sequence motif that promotes active platelet aggregation. The RGD motif containing GBP may contain a single repeat of the RGD motif or may contain multiple repeats of the RGD motif, such as, for example, 2, or 5, or 10 or more repeats of the RGD motif. One of skill in the art will understand that conservative substitutions of particular amino acid residues of the RGD motif containing GBPs may be used so long as the RGD motif containing GBP retains the ability to bind comparably as the native RGD motif. One of skill in the art will also understand that conservative substitutions of particular amino acid residues flanking the RGD motif so long as the RGD motif containing GBP retains the ability to bind comparably as the native RGD motif.

In some embodiments, the GBP can include a cyclic RGD (cRGD) peptide having the amino acid sequence of cyclo-CNPRGDY(OEt)RC (SEQ ID NO: 3). A cyclic peptide having SEQ ID NO: 3 can have high selectivity and affinity to GPIIb-IIIa on activated platelets but do not bind or activate quiescent platelets nor interact with other RGD-binding integrins. The RPP like the VBP and CBP can be synthesized using FMoc-based solid phase chemistry on Knorr resin, and characterized using mass spectroscopy.

Advantageously, the VBPs, CBPs, and GPBs can each include about 5 to about 30 amino acids. By limiting the size of the peptides to about 5 to about 30 amino acids, the VBPs, CBPs, and GBPs can be spatially or topographically arranged on the flexible nanoparticle surface such that the VBPs, CBPs, and GBPs do not spatially mask each other and are able to adhere to a vascular surface, vascular disease site, and/or vascular injury site with exposed vWF and collagen and promote arrest and aggregation of active platelets onto sites of the synthetic platelet adhesion.

The VBPs, CBPs, and GBPs can be conjugated to the nanoparticle surface by reacting the peptides with through their N-termini to the carboxyl termini of a heterobifunctional PEG, such as maleimide-PEG-COOH. The PEG-peptide conjugates or PEGylated peptides can then be conjugated to the nanoparticle using known conjugation techniques.

The PEG molecules can have a variety of lengths and molecular weights, including, for example, PEG 200, PEG 1000, PEG 1500, PEG 4600, PEG 10,000, or combinations thereof. In other embodiments, the VBPs, CBPs, and GBPs can be conjugated to the nanoparticle surface with PEG acrylate, or PEG diacrylate, molecules of a variety of molecular weights.

In one example, the VBPs, CBPs, and GBPs can be reacted with maleimide-PEG-COOH to form Mal-PEG-peptide conjugates. SA/PAH nanoparticles with albumin as the outermost layer can then be treated with dithiothreitol (DTT) to introduce a high density of sulfhydryl (—SH) groups on the surface. The Mal-PEG-peptides can then be incubated with the DTT-treated nanoparticles, such that the MAL termini can react with the free —SH groups to form particles decorated with various peptides presented on the particle surface via PEG linkers.

The ratio of VPBs to CPBs provided on the nanoparticle surface can be about 70:30 to about 30:70 and be adjusted accordingly to maximize adhesion under low-to-high shear conditions. In some embodiments, the ratio of VPB:CPB:GBP can be about 1:1:2 to 1:2:1 to 2:1:1. It will be appreciated, that other ratios can be used to enhance the nanoparticle adherence and activated platelet aggregation.

In some embodiments, the compositions comprising a synthetic platelet described herein, can be formulated and administered to an animal, preferably a human, in need of reducing or slowing blood loss. In other embodiments, the compositions comprising a synthetic platelet described herein, may be formulated and administered to an animal, preferably a human, to facilitate the delivery of a therapeutic agent.

In some embodiments, the synthetic platelets described herein can be provided in a pharmaceutical composition. Such a pharmaceutical composition may consist of a synthetic platelet alone, in a form suitable for administration to a subject, or the pharmaceutical composition may comprise a synthetic platelet and one or more pharmaceutically acceptable carriers, one or more additional ingredients, one or more pharmaceutically acceptable therapeutic agents, bioactive agents, diagnostic agents, or some combination of these. The therapeutic agent may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the therapeutic agent may be combined and which, following the combination, can be used to administer the therapeutic agent to a subject.

As used herein, the term "physiologically acceptable" ester or salt means an ester or salt form of the therapeutic agent which is compatible with any other ingredients of the pharmaceutical composition, which is not deleterious to the subject to which the composition is to be administered.

In some embodiments, the bioactive agent, diagnostic agent, and/or therapeutic agent can be conjugated, encapsulated, and/or contained with the synthetic platelet so that synthetic platelet acts as a delivery vehicle. In other embodiments, the bioactive agent, diagnostic agent, and/or therapeutic agent can be merely contained in a pharmaceutical composition either with or without the synthetic platelets and administered to concurrently with or separately from administration of the synthetic platelets. Selection of a bioactive agent, diagnostic agent, and/or therapeutic agent to be conjugated to or encapsulated within the synthetic platelet is dependent upon the use of the synthetic platelet and/or the condition being treated and the site and route of administration.

Bioactive agents encapsulated by and/or conjugated to the synthetic platelet can include any substance capable of exerting a biological effect in vitro and/or in vivo. Examples of bioactive agents can include, but are not limited to, biologically active ligands, small molecules, DNA fragments, DNA plasmids, interfering RNA molecules, such as siRNAs, oligonucleotides, and DNA encoding for shRNA. Diagnostic agents can include any substance that may be used for imaging a region of interest (ROI) in a subject and/or diagnosing the presence or absence of a disease or diseased tissue in a subject. Therapeutic agents can refer to any therapeutic or prophylactic agent used in the treatment (including the prevention, diagnosis, alleviation, or cure) of a malady, affliction, condition, disease or injury in a subject. It will be appreciated that the membrane can additionally or optionally include proteins, carbohydrates, polymers, surfactants, and/or other membrane stabilizing materials, any one or combination of which may be natural, synthetic, or semisynthetic.

The methods of treatment using the synthetic platelets described herein include administering a therapeutically effective amount of a synthetic platelet to a subject in need thereof. It should be understood, that the methods of treatment by the delivery of a synthetic platelet include the treatment of subjects that are already bleeding, as well as prophylactic treatment uses in subjects not yet bleeding. In a preferred embodiment the subject is an animal. In a more preferred embodiment the subject is a human.

The embodiments described herein should in no way be construed to be limited to the synthetic platelets described herein, but rather should be construed to encompass the use of additional synthetic platelets, both known and unknown, that diminish or reduce bleeding or blood loss.

The formulations of the pharmaceutical compositions described herein may be prepared by any method known or hereafter developed in the art of pharmacology. In general, such preparatory methods include the step of bringing a synthetic platelet into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions, which are suitable for ethical administration to humans, it will be understood by the skilled artisan that such compositions are generally for administration to animals of all sorts. Modification of pharmaceutical compositions for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, animals including commercially relevant animals such as cattle, pigs, horses, sheep, cats, and dogs, birds including commercially relevant birds such as chickens, ducks, geese, and turkeys.

Pharmaceutical compositions that are useful in the methods described herein may be administered, prepared, packaged, and/or sold in formulations for parenteral, oral, rectal, vaginal, topical, transdermal, pulmonary, intranasal, buccal, ophthalmic, or another route of administration.

The compositions described herein may be administered via numerous routes, including, but not limited to, parenteral, oral, rectal, vaginal, topical, transdermal, pulmonary, intranasal, buccal, or ophthalmic administration routes. The route(s) of administration will be readily apparent to the skilled artisan and will depend upon any number of factors including the type and severity of the disorder being treated, the type and age of the veterinary or human patient being treated, and the like.

Parenteral administration of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition on or through a surgical incision, by application of the composition on or through a tissue-penetrating non-surgical wound, and the like. In particular, parenteral administration is contemplated to include, but is not limited to, cutaneous, subcutaneous, intraperitoneal, intramuscular, intrasternal injection, intravenous, and intra-arterial.

Formulations of a pharmaceutical composition suitable for parenteral administration comprise the therapeutic agent combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi dose containers containing a preservative. Formulations for parenteral administration include, but are not limited to, suspensions, solutions, emulsions in oily or aqueous vehicles. Such formulations may further comprise one or more additional ingredients including, but not limited to, suspending, stabilizing, or dispersing agents. In one embodiment of a formulation for parenteral administration, the therapeutic agent is provided in dry (i.e., powder or granular) form for reconstitution with a suitable vehicle (e.g., sterile pyrogen free water) prior to parenteral administration of the reconstituted composition.

Pharmaceutical compositions that are useful in the methods described herein may be administered systemically in oral solid formulations, ophthalmic, suppository, aerosol, topical or other similar formulations. In addition to the compound such as heparin sulfate, or a biological equivalent thereof, such pharmaceutical compositions may contain pharmaceutically acceptable carriers and other ingredients known to enhance and facilitate administration.

The pharmaceutical compositions described herein may also be formulated so as to provide slow, prolonged or controlled release. In general, a controlled-release preparation is a pharmaceutical composition capable of releasing the synthetic platelet at a desired or required rate to maintain constant activity for a desired or required period of time.

A pharmaceutical composition described herein may be prepared, packaged, or sold in bulk, as a single unit dose, or as a plurality of single unit doses. As used herein, a "unit dose" is discrete amount of the pharmaceutical composition comprising a predetermined amount of the activity. The amount of the activity is generally equal to the dosage, which would be administered to a subject or a convenient fraction of such a dosage such as, for example, one-half or one-third of such a dosage.

The relative amounts of the ingredients in a pharmaceutical composition of the invention will vary, depending upon the identity, size, and condition of the subject treated and further depending upon the route by which the composition is to be administered. By way of a non-limiting example, the composition may comprise between 0.1% and 100% (w/w) of the synthetic platelets.

The synthetic platelet compositions described herein may be administered to deliver a dose of between 1 ng/kg/day and 100 mg/kg/day. In one embodiment, a dose can be administered that results in a concentration of the synthetic platelets between 1 µM and 10 µM in a mammal. While the precise dosage administered will vary depending upon any number of factors, including but not limited to, the type of animal, the amount of bleeding being treated, the type of bleeding being treated, the type of wound being treated, the age of the animal and the route of administration. Preferably, the dosage of the synthetic platelet will vary from about 1 µg to about 50 mg per kilogram of body weight of the animal. More preferably, the dosage will vary from about 10 µg to about 15 mg per kilogram of body weight of the animal. Even more preferably, the dosage will vary from about 100 µg to about 10 mg per kilogram of weight of the animal.

The pharmaceutical compositions may be prepared, packaged, or sold in the form of a sterile injectable aqueous or oily suspension or solution. This suspension or solution may be formulated according to the known art, and may comprise, in addition to the therapeutic agent, additional ingredients such as the dispersing agents, wetting agents, or suspending agents described herein. Such sterile injectable formulations may be prepared using a non-toxic parenterally acceptable diluent or solvent, such as water or 1,3 butane diol, for example. Other acceptable diluents and solvents include, but are not limited to, Ringer's solution, isotonic sodium chloride solution, and fixed oils such as synthetic mono or di-glycerides.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

The pharmaceutical composition may be administered to an animal as needed. The pharmaceutical composition may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

EXAMPLES

The application is further described in detail by reference to the following examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1

Past approaches on mimicking platelet's hemostasis-relevant functions on synthetic platforms have mainly focused on amplifying platelet's 'aggregation' functionality by decorating synthetic particle surfaces with aggregation-promoting biomolecules like Fibrinogen (Fg) or Fg-derived peptide sequences. For example, synthetic particle platforms like liposomes, albumin spheres and synthetic polymeric particles have been surface-decorated with platelet membrane-derived glycoproteins, Fg, Fg-derived Arginine-Glycine-Aspartic Acid (RGD) peptides and Fg-derived H12 dodecapeptides. All of these are essentially various designs of 'super-fibrinogen' particles that can amplify the aggregation of active platelets due to their increased surface-valency of platelet-bridging motifs (i.e., Fg or Fg-derived peptides), compared to hexavalent Fg itself. However, in natural primary hemostasis, platelet aggregation is preceded by stable platelet adhesion at the injury site under blood flow, as shown in FIG. 1.

Platelet adhesion is mediated by shear-dependent binding of the GPIba extracellular domain of the platelet surface glycoprotein GPIb/IX/V complex with von Willebrand factor (vWF) secreted from the injured endothelium, augmented by binding of platelet surface glycoproteins GPIa/IIa and GPVI to sub-endothelial collagen. The vWF-binding helps in the initial arrest and rolling of platelets at the injury site, while collagen binding stabilizes the adhered platelets under the hemodynamic flow environment. These adhesion mechanisms result in platelet activation signaling, ultimately leading to a ligand-binding conformational change of the platelet surface integrin GPIIb-IIIa that then binds to Fg to promote aggregation of the activated platelets to form the primary hemostatic plug.

In this example, we show bioengineering of synthetic constructs where vWF-binding and collagen-binding ligand motifs are integrated on the same particle (FIG. 2), and investigate their platelet-mimetic adhesive capabilities under physiologically relevant flow environment (wall shear stresses) in vitro, using a parallel plate flow chamber (PPFC). For vWF-binding, we have investigated a small synthetic peptide with amino acid sequence TRYLRIHPQSWVHQI (SEQ ID NO: 1), that is derived from the C2 domain (residues 2303-2332) of the coagulation factor FVIII which is known to form complex with vWF prior to thrombin or factor Xa catalyzed activation in the coagulation cascade. We have compared the vWF-binding of liposomes surface-decorated with this vWF-binding peptide (VBP) to liposomes surface-decorated with the previously reported recombinant GPIbα fragment. For collagen binding, we have investigated a short 7-repeat of the Glycine(G)-Proline(P)-Hydroxyproline(O) tri-peptide (i.e., -[GPO]$_7$-), with helicogenic affinity to fibrillar collagen. This small collagen-binding peptide (CBP) can promote adhesion to fibrillar collagen, but cannot activate quiescent platelets due to absence of long triple-helical conformation. We have demonstrated that that the vWF-binding constructs undergo enhanced adhesion under increasing wall shear, while the collagen-binding constructs undergo stable adhesion in an apparent shear-independent fashion. Furthermore, we have integrated simultaneous vWF-binding and collagen-binding motifs on the same liposome platform and have investigated their adhesion capability to a vWF/collagen mixed surface under flow, in vitro. In such heteromultivalent liposome surface decoration, we have demonstrated that the platelet-mimetic dual adhesion mechanisms (simultaneous vWF-binding and collagen-binding) can be successfully achieved provided the vWF-binding and the collagen-binding ligand motifs do not spatially interfere each other while conjugated onto the liposome surface. Altogether, by surface engineering of liposomes via decoration of specific ligands, we demonstrate efficient molecular mimicry of platelet's dual adhesion mechanisms. This approach can be potentially adapted to various particle platforms to optimize the design of a platelet-mimetic synthetic bioconjugate construct.

Materials

Cholesterol, Dimethyl Sulfoxide (DMSO) and collagen were purchased from Sigma Aldrich (St. Louis, Mo., USA). The lipids Distearyl Phosphatidyl Choline (DSPC), 2000 M W Polyethylene glycol-modified Distearyl Phosphatidyl Ethanolamine (DSPE-PEG$_{2000}$), and Carboxy-terminated Polyethylene glycol-modified DSPE (DSPE-PEG$_{2000}$-COOH) were purchased from Avanti Polar Lipids (Alabaster, Ala., USA). Human vWF (FXIII free) was purchased from Hematologic Technologies Incorporation (Essex Jn, Vt., USA). The Parallel Plate Flow Chamber (PPFC) system was purchased from Glycotech (Gaithersburg, Md., USA).

Ligand Motifs vWF-Binding Motifs

For vWF binding, a recombinant GPIbα fragment (rGPIbα) containing the vWF binding sites (residues 1 to 302) or a short chain vWF-binding peptide (VBP) was used. The GPIbα fragment was expressed in CHO cells and isolated, adapting methods described by Murata et al. The VBP, TRYLRIHPQSWVHQI, was synthesized using Fluorenylmethyloxycarbonyl chloride (FMoc)-based solid phase chemistry on Knorr resin, and characterized using mass spectroscopy. Each vWF molecule has only one binding region for this peptide, and hence we rationalized that pre-coated vWF surface or shear-enhanced multimerization of vWF on collagen-coated surface will present multiple binding sites for multiple copies of this peptide decorated on the liposome surface, thereby providing a mechanism for enhanced adhesion of the liposomes with increasing shear.

Collagen-Binding Motifs

The CBP, [GPO]7, was also synthesized using FMoc-based solid phase chemistry on Knorr resin, and characterized using mass spectroscopy. The GPO trimer is based on amino acid repeats found in the native collagen structure. It has been reported that the activation of platelets usually caused by interaction with collagen through GPVI and GPIa/IIa, can also potentially occur when platelets interact with collagen-derived peptides. This can be a potential problem regarding decorating synthetic particle surfaces with collagen-derived peptides for binding of collagen, because in vivo the constructs can potentially interact with quiescent blood platelets and systemically activate them, posing thromboembolic risks. However, it has been reported that interaction of platelet receptors with collagen and the subsequent platelet activation mechanisms are dependent upon receptor clustering induced by multimeric long chain triple-helical fibrillar collagen and not by short collagen-mimetic peptide repeats. In fact, it has been shown that GPO-trimer repeats as high as a 30-mer (10 repeats) only partially interact with platelet GPIa/IIa and GPVI integrins and are incapable of activating platelets; yet they can effectively bind to fibrillar collagen via helicogenic interaction. Hence, we rationalized that our 7-mer short chain monomeric CBP will not activate quiescent platelets in circulation but can still allow binding of CBP-decorated liposomes to collagen covered surface, under flow.

The mass spectrometric characterization data of the peptides are available in the Supporting Information. Also, the inability of both VBP and CBP to activate platelets was confirmed by aggregometry, and this data is also available in the Supporting Information.

Ligand-Modified Liposomal Construct Fabrication

The rGPIbα, VBP or CBP were conjugated to DSPE-PEG-COOH using carbodiimide-mediated amidation chemistry to form DSPE-PEG-ligand molecules, utilizing previously reported methods. To fluorescently label the liposomes, DSPE-Fluorescein (green fluorescence, $\lambda$max~530 nm) was synthesized by reacting the free amine (—NH2) termini of DSPE with NHS-Fluorescein at basic pH. Specific proportions of the DSPE-PEG-rGPIb$\alpha$, DSPE-PEG-VBP or DSPE-PEGCBP were combined with unmodified DSPE-PEG, DSPC, cholesterol, and DSPE-Fluorescein to fabricate peptide-decorated green fluorescent liposomal constructs, using the standard reverse phase evaporation and extrusion technique. The liposome size distribution, characterized using dynamic light scattering (DLS), was found to be ~150 nm (c.f. Supporting Information).

Parallel Plate Flow Chamber (PPFC)

The PPFC setup is appropriate for biomolecular interaction analysis under a dynamic shear flow environment. In the PPFC, by maintaining Renyold's number in the 'laminar' range (~$10^5$), the wall shear stress can be modulated as a function of flow rate (Q) by:

$$\tau_w = \frac{6\mu Q}{bh^2} \quad (1)$$

where $\mu$=fluid viscosity, b=width of the chamber, and h=distance between plates. For our experiments, b/h was >20 and Q was maintained to provide $\tau_w$ in the range of 5-55 dynes/cm2, which covers a substantial range of physiological shear in blood flow (52). Distinct circular areas on glass slides were coated with collagen, vWF or 50:50 mixture of vWF:collagen (test surfaces) and Bovine Serum Albumin (BSA, negative control surface with no adhesion specificity). The coated slides were vacuum-sealed into the PPFC for subsequent experiments.

Platelet-Mimetic Adhesion Studies Under Flow In Vitro

For studying platelet-mimetic vWF-adhesive functionality, 5 mol % DSPE-PEG-rGPIb$\alpha$ or DSPE-PEG-VBP was combined with DSPC (49 mol %), cholesterol (40 mol %), DSPE-PEG (5 mol %), and DSPE-Fluorescein (1 mol %) to form the final liposomal construct. The fluorescein labeled (green fluorescent, $\lambda$max=530 nm) liposomes, at a concentration of 10 µM total lipid, were allowed to flow through the PPFC in a closed loop over vWF-coated and BSA-coated surface under various flow rates to produce wall shear stresses from 5-55 dynes/cm$^2$ for 30 mins. After 30 minutes, flow of just PBS was maintained in an open loop for an additional 15 minutes in order to remove any loosely bound constructs and gain insight on the adhesion stability and retention of the constructs on the test and control surfaces. The slides were imaged at various time points (5, 15, 30, and 45 mins) of flow in the PPFC, using an inverted epifluorescence microscope (Carl Zeiss Axio Observer D1) with a photometrics chilled CCD camera (Axiocam MRM) and a 63× objective. Images were collected using Axiovision™ software with fixed exposure times of 400 ms. From each image, extent of adhesion and retention was quantified by measuring surface-averaged fluorescence intensity using the Axiovision software. Statistical analysis of fluorescence intensity was performed using ANOVA and significance was considered as $p<0.05$. FIG. 3A shows a schematic view of the PPFC experimental set-up and the expected interaction of the vWF-binding liposomal constructs with the test and control surface regions. In an additional experimental design, we aimed to investigate if soluble vWF could adhere to collagen and multimerize under high shear stress, and then induce adhesion of VBP decorated liposomes. This is inspired by the natural physiological mechanism where soluble vWF adheres to exposed sub-endothelial collagen, multimerizes under shear and subsequently allows adhesion of platelets via interaction with platelet surface GPIb$\alpha$. For this, green fluorescent VBP-modified liposomes and soluble FVIII-free human vWF were introduced into the PPFC and allowed to flow over collagen-coated surface or albumin-coated surface under high shear stress of 55 dynes/cm$^2$ for 5-30 min and the adhesion of the liposomes over time was imaged with epifluorescence microscopy using the microscope set-up described previously.

For studying platelet-mimetic collagen-adhesive functionality, 5 mol % DSPE-PEG-CBP was combined with DSPC (49 mol %), cholesterol (40 mol %), DSPE-PEG (5 mol %), and DSPEFluorescein (1 mol %) to form the final liposomal construct. These fluorescently labeled liposomes were allowed to flow through the PPFC over collagen-coated and BSA-coated surfaces in the same way as VBP-decorated liposomes, i.e., 30 min in closed loop followed by 15 min open loop circulation of just PBS. Imaging at various time points and image analysis were carried out as before. FIG. 5A shows a schematic view of the PPFC experimental set-up and the expected interaction of the CBP-decorated liposomes with the test and control surfaces.

For studying cumulative effects of simultaneous vWF and collagen-binding, 2.5 mol % DSPEPEG-rGPIb$\alpha$ or DSPE-PEG-VBP and 2.5 mol % of CBP were combined with DSPC (49 mol %), cholesterol (40 mol %), DSPE-PEG (5 mol %), and DSPE-Fluorescein (1 mol %) to form the final heteromultivalently decorated liposomal constructs. These fluorescently labeled liposomes were allowed to flow in the PPFC over a surface coated with 50:50 vWF:collagen (mixed coating) under 5-55 dyn/cm$^2$ shear stress, and the imaging and image analysis were carried out as before.

For all adhesion studies, besides testing the interaction of ligand-modified liposomes on negative control albumin surfaces, additional control studies were also carried out by testing unmodified (no surface decoration) liposomes on vWF-coated, collagen-coated or mixed-coated surfaces.

Results

Platelet-Mimetic vWF Adhesion of Ligand-Decorated Liposomes Under Flow In-Vitro

Figure 3C:
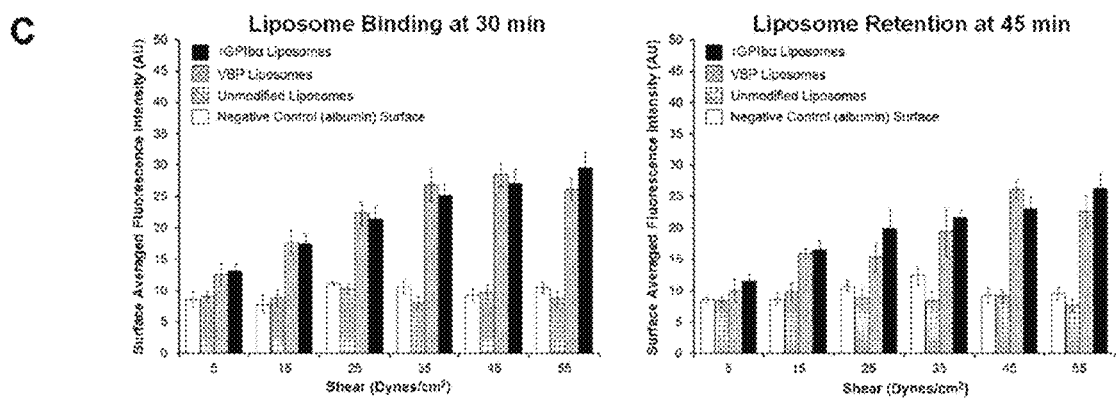
FIGS. 3(A-C) illustrate representative results from PPFC studies using rGPIbα- or VBP-decorated liposomal constructs allowed to flow over vWF-coated surface versus albumin surface. (A) schematic of experimental set-up; (B) the ligand-modified liposomes showed minimal adhesion or retention on albumin surface and the unmodified liposomes showed minimal adhesion or retention on vWF surface, whereas the rGPIbα-modified and the VBP-modified liposomes both showed significant adhesion and retention on vWF surface under flow; (C) quantitative analysis of the adhesion (at 30 min) and retention (at 45 min) data using surface-averaged fluorescence intensity shows that both rGPIbα-modified and VBP-modified liposomes undergo increasing adhesion and retention on vWF surface under increasing shear, mimicking the vWF-binding of platelets.

FIG. 3B shows a representative set of fluorescence images from PPFC experiments using rGPIb$\alpha$-decorated liposomes and VBP-decorated liposomes on vWF-coated surfaces versus albumin-coated surfaces under flow. Although images were taken at six shear values between 5-55 dynes/cm$^2$ and at four time points during flow between 5-45 mins for each of the liposomal constructs, representative fluorescent images are shown at only two shear values (5 and 35 dynes/cm$^2$) and two time points (30 and 45 minutes) for convenience. FIG. 3C shows the quantitative analysis of surface-averaged fluorescence intensity values from the adhesion of the various liposomal constructs on vWF-coated surfaces over the entire shear stress range at 30 minutes and 45 minutes. Statistical analysis of fluorescence intensity values shows that both rGPIb$\alpha$-decorated and VBP-decorated liposomal constructs undergo increased adhesion on the vWF-coated surfaces with increasing shear, while on albumin-coated surfaces both types of constructs showed only minimal adhesion irrespective of shear stress values. In addition, the unmodified liposomes showed minimal adhesion to vWF at all shear stress ranges.

Figure 4:
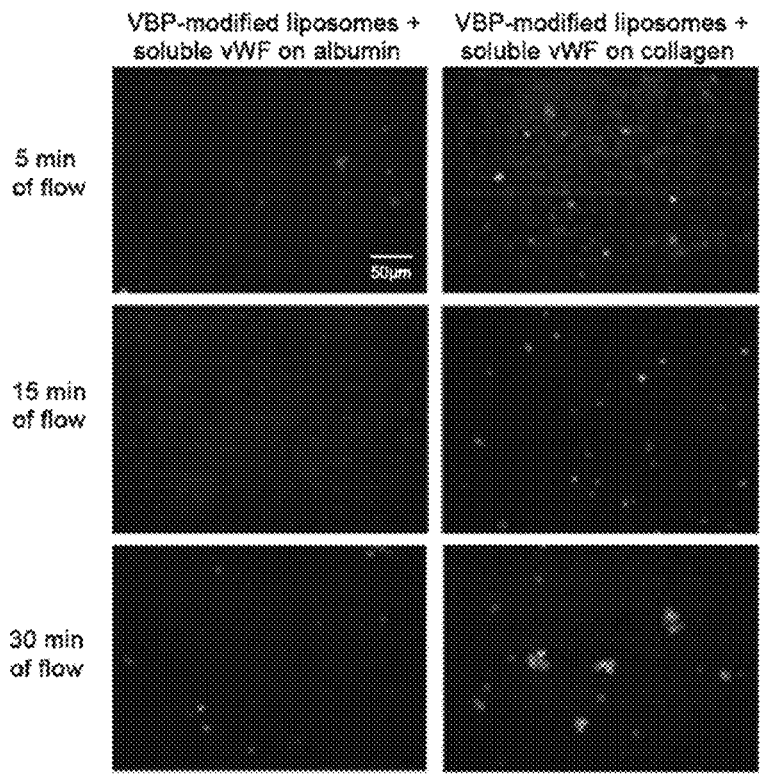

FIG. 4 shows representative fluorescent images from the additional experimental design involving flow of soluble vWF and VBP-modified liposomes over collagen or albumin surface under high shear stress. Representative results are shown for a shear stress value of 55 dynes/cm² for three time-points of 5 min, 15 min and 30 min of flow. As evident from the results, green fluorescent VBP-modified liposomes are able to adhere when introduced along with soluble vWF to flow over a collagen-coated surface, but not on an albumin-coated surface. Furthermore, the VBP-modified liposomes seemed to undergo enhanced amount of adhesion (larger fluorescent 'patch' areas) with time, under the high shear value.

Figure 5C:
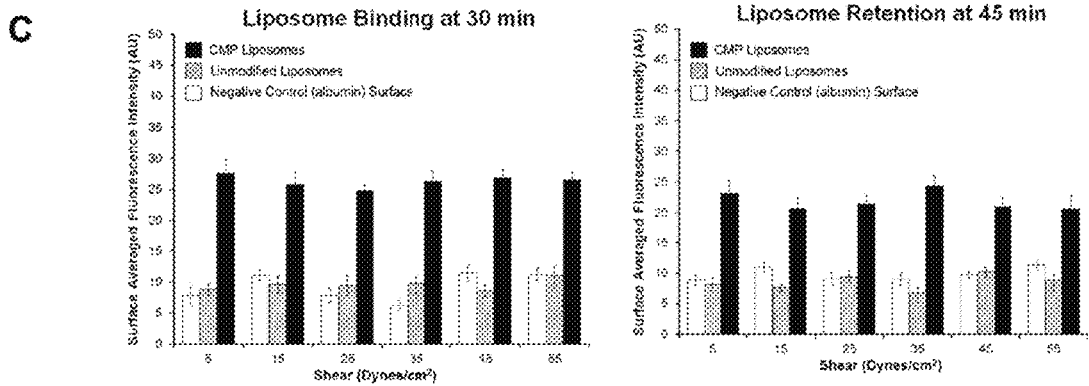

Platelet-Mimetic Collagen Adhesion of Ligand-Decorated Liposomes Under Flow In-Vitro FIG. 5B shows a representative set of fluorescence images from PPFC experiments using CBP decorated liposomes on collagen-coated surfaces versus albumin-coated surfaces under flow. As before, the representative images are shown at only two shear values (5 and 35 dynes/cm²) and two time points (30 and 45 minutes) for convenience. FIG. 5C shows quantitative analysis of the surface-averaged fluorescence intensity values from the adhesion of the various liposomal constructs on collagen-coated surfaces over the entire shear stress range at 30 min and 45 min. Statistical analysis of fluorescence intensity measurements shows the CBP-decorated liposomal constructs undergo significant adhesion to collagen-coated surfaces under flow with no apparent shear-dependent effect, but minimal adhesion to albumin surfaces. In addition, the unmodified constructs showed minimal adhesion on collagen surfaces.

Figure 6A:
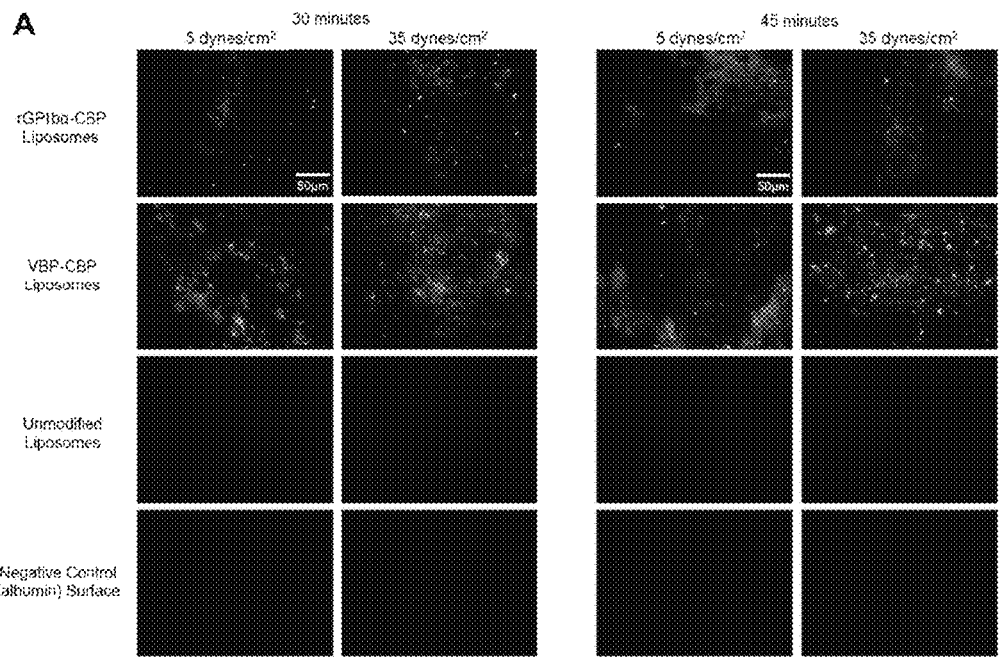
Figure 6B:
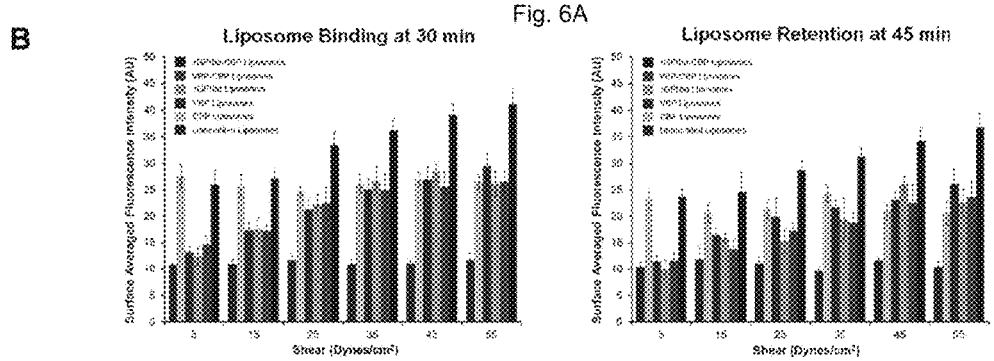

Combining vWF-Adhesion and Collagen Adhesion on the Surface of Liposomes In Vitro FIG. 6A shows representative set of fluorescence images for adhesion of liposomes surface decorated with both rGPIbα and CBP (2.5 mol % each), or both VBP and CBP (2.5 mol % each), onto a mixed coated (vWF:collagen 50:50) surface under flow in the PPFC. The adhesion of unmodified liposomes on these mixed coated surfaces and the adhesion of the ligand-modified liposomes on the negative control (albumin) surfaces are also shown in the figure for comparison. As before, the representative images are shown at only two shear values (5 and 35 dynes/cm²) and two time points (30 and 45 minutes) for convenience. FIG. 6B shows the quantitative analyses of the fluorescence intensity data from the adhesion of the various heteromultivalent liposomal constructs over the entire shear stress range, compared with the adhesion data for liposomes bearing rGPIbα-decorations only, VBP-decorations only and CBP decorations only, all on mixed coated (vWF: collagen 50:50) surfaces. As evident from the fluorescent images, as well as, the quantitative data, liposomes bearing both rGPIbα and CMP showed enhanced adhesion on the mixed coated surface with increasing shear, but this was not statistically different from liposomes bearing rGPIbα modification alone. In comparison, liposomes bearing both VBP and CBP not only showed enhanced adhesion to the mixed coated surface under increasing shear, but the levels of adhesion were significantly higher than liposomes bearing VBP decoration or CBP decoration alone.

Our results indicate that the shear-dependent enhancement in adhesion of the rGPIbα-decorated or VBP-decorated liposomal constructs were due to specific interactions of the ligands to the vWF surface, since the same liposomes showed only minimum adhesion on albumin surfaces. Furthermore, the results from experiments with VBP-decorated liposomes and soluble vWF under flow on collagen surfaces suggest that possible multimerization of the soluble vWF with time on the collagen surface under high shear allows increased adhesion of VBP-decorated liposomes on the vWF-rich areas, as indicated by formation of larger fluorescent patches with time. Altogether, these results demonstrate successful mimicry of shear-dependent platelet adhesion to vWF using surface-engineered liposomes. The results from interaction of CBP-decorated liposomes on collagen-coated surface indicate that the adhesion is mostly shear-independent and is due to specific helicogenic interaction of the CBP with collagen. Hence, these data establish successful mimicry of the collagen-binding property of platelets with CBP-decorated liposomes. Analysis of the results from experiments with liposomes simultaneously bearing vWF-binding and collagen-binding motifs suggest that when decorated simultaneously on the liposomal surface, the larger rGPIbα motif (~300 amino acid residues) possibly masks the much smaller CBP motif (~21 residues), thereby preventing the combination effect of simultaneous vWF-binding and collagen-binding by the liposomes. The resultant adhesion seems to happen principally due to only rGPIbα-vWF interaction in a shear-dependent fashion. In contrast, when VBP (~15 amino acid residues) is used in conjunction with CBP for liposome surface decoration, these two small peptides possibly do not mask each other's specific interactions and therefore a combined effect of vWF-binding and collagen-binding becomes evident in the enhanced adhesion of the heteromultivalent liposomal constructs on the mixed coated surfaces under flow. Hence we demonstrate that by decorating a synthetic particle (liposome) surface with ligands binding simultaneously to vWF and collagen, and ensuring that the decorated ligands do not spatially mask each other, we can successfully mimic the hemostatically relevant dual adhesion mechanisms of platelets.

The functional biomimetic design of a platelet-mimetic synthetic construct should incorporate both the 'adhesion' functionalities and the 'aggregation' functionalities of natural platelets. We envision that platelet-mimetic hemostatic efficacy of synthetic constructs can be further enhanced if the 'aggregation'-promoting component and 'adhesion'-promoting component can be combined on the same particle. Therefore, in subsequent studies, we will combine the adhesion-promoting VBP and CBP motifs along with aggregation-promoting Fg-mimetic RGD peptide motifs on the same liposome, and investigate whether these functionally integrated constructs can themselves adhere to vWF/collagen surfaces under flow and promote recruitment and aggregation of platelets at the sites of liposome adhesion.

It is to be noted that the model particle used in our studies were spherical unilamellar liposomes about 150 nm in diameter. Several recent mathematical modeling and experimental studies have demonstrated that there exist significant correlations between the shape and size of particles to their location in hemodynamically relevant flow patterns. For natural platelets, their hemostatic functions at the vessel wall depend upon their ability of 'margination' to the wall injury site through RBCs and other blood components. This hemodynamic migration is significantly influenced by platelet's shape and size. Based on such observations, we can show an additional component of synthetic platelet design will optimization of particle geometry (size and shape) that can facilitate enhanced wall-margination of the particles. An ideal biomimetic design of a synthetic platelet can be achieved by integration of margination favoring optimal physical parameters (size and shape) with adhesion- and aggregation-promoting optimal biological parameters (chemistry and density of ligand modifications). Also, these design components and resultant insight can provide novel avenues to target such particles as efficient drug delivery vehicles to vascular disease sites with exposed vWF or collagen.

Example 2

We describe in this example the development and experimental results from integrating platelet-mimetic adhesion- and aggregation-promoting functionalities on a single particle, by decorating the surface of 150 nm diameter liposomes simultaneously with three peptides, a vWF-binding peptide (VBP), a collagen-binding peptide (CBP) and an active platelet GPM-Ina-binding peptide (cRGD). We have previously demonstrated in Example 1 that liposomes bearing VBP and CBP motifs undergo platelet-mimetic adhesion under flow on vWF and collagen-coated surfaces in vitro at low-to-high shear, in parallel plate flow chamber (PPFC) experiments. Here, we demonstrate that cRGD-modified liposomes pre-adhered to a surface can enhance the aggregation of ADP-activated platelets onto them, even at a low platelet concentrations. Subsequently, we demonstrate that liposomes bearing all three peptides (VBP, CBP and cRGD), when introduced in PPFC flow along with low concentration of ADP-activated platelets over a vWF/collagen mixed coated surface, are able to adhere to the surface under high shear and promote arrest and aggregation of active platelets onto sites of liposome adhesion.

Materials and Methods

Materials

Phosphate Buffered Saline (PBS), 3.8% w/v sodium citrate, parformaldehyde (PFA), Avidin, Bovine Serum Albumin (BSA), and ethanol were purchased from Thermo Fisher Scientific (Pittsburgh, Pa., USA). Cholesterol, Dimethyl Sulfoxide (DMSO), and collagen were purchased from Sigma Aldrich (St. Louis, Mo., USA). Fluorescently labeled monoclonal antibody, AlexaFluor® 647-anti-CD62P (staining activated platelet P-selectin), was purchased from BioLegend (San Diego, Calif., USA). The lipids Distearyl Phosphatidyl Choline (DSPC), Distearyl Phosphatidyl Ethanolamine (DSPE), Polyethylene Glycol-modified DSPE (DSPE-PEG2000), Carboxy-polyethylene Glycol-modified DSPE (DSPE-PEG2000-COOH), and Biotinylated Polyethylene Glycol-modified DSPE (DSPE-PEG2000-Biotin) were purchased from Avanti Polar Lipids (Alabaster, Ala., USA). ClearOx® and N-Hydroxysuccinimide-modified Fluorescein (NHS-Fluorescein) was purchased from Invitrogen Corporation (Carlsbad, Calif., USA). Human vWF (FXIII free) was purchased from Hematologic Technologies Incorporation (Essex Jn, Vt., USA). The Parallel Plate Flow Chamber (PPFC) system for dynamic flow studies was purchased from Glycotech (Gaithersburg, Md., USA). The peptide sequences used were TRYLRIHPQSWVHQI (VBP), (SEQ ID NO: 1), [GPO]$_7$ (CBP) (SEQ ID NO: 2), and cyclo-CNPRGDY(OEt)RC (cRGD) (SEQ ID NO: 3). The VBP, CBP and the linear precursor of the cRGD peptide were synthesized using Fluorenylmethyloxycarbonyl chloride (FMoc)-based solid phase chemistry on Knorr resin and characterized using mass spectroscopy. The linear precursor of cRGD was subjected to sulfhydril oxidation of Cysteine termini using ClearOx® reagent, to achieve disulphide-based cyclization.

Preparation of Platelet Suspensions

Venous blood from healthy, medication-free, adult donors was drawn into 3.8% w/v sodium citrate anticoagulant at a 9:1 ratio (by volume), in compliance with CWRU IRB-approved protocols. Platelet Rich Plasma (PRP) was obtained by centrifuging the human whole blood at 150 g for 15 min and platelet count was monitored using a Coulter Counter. In order to prepare thrombocytopenic condition-mimicking low platelet concentrations (LPC), a portion of PRP was further centrifuged at 2500 g for 25 mins, to obtain platelet-poor plasma (PPP). This PPP was then added volumetrically to PRP such that final platelet concentration was adjusted to ~20,000/μl, as monitored by Coulter Counter. These LPC suspensions were used immediately.

Fabrication of Surface-Modified Liposomes

Figure 7:
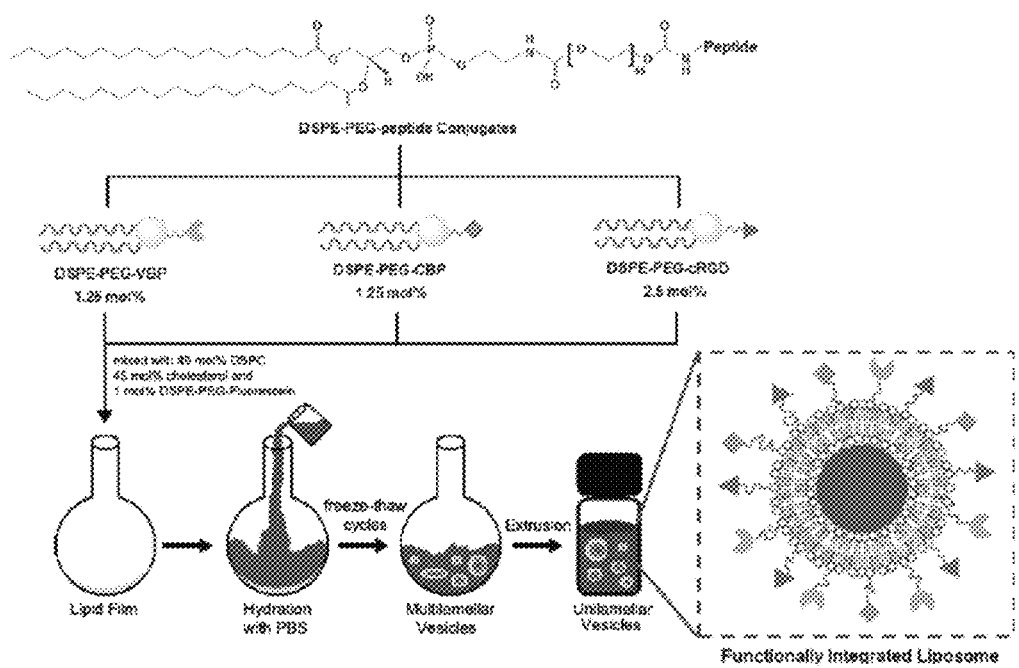

The VBP, CBP and cRGD peptides were conjugated via their N-termini to the carboxyl terminus of DSPE-PEG$_{2000}$-COOH via standard carbodiimide chemistry adapting previously reported methods, resulting in the various DSPE-PEG-peptide molecules. NHS-Fluorescein was reacted with DSPE-PEG$_{2000}$-COOH to form DSPE-PEG-fluorescein for fluorescent labeling of liposomes. DSPE-PEG-peptides were mixed at specific mol % with DSPC, cholesterol, DSPEPEG, DSPE-PEG-Biotin and DSPE-PEG-fluorescein as needed and such mixed lipid formulations were used towards fabricating liposomes via standard reverse phase evaporation and extrusion technique. The extrusions were carried out near the transition temperature of DSPC (~60° C.) through nanoporous (200 nm pore-size) polycarbonate membranes, resulting in unilamellar liposomal constructs of ~150 nm average diameter. A general schematic of fabricating the 'functionally integrated' liposomes (simultaneously bearing all three peptides VBP, CBP and cRGD) is shown in FIG. 7.

In-Vitro Platelet Aggregation Studies

For studying whether the cRGD-modified liposomal constructs pre-adhered to a surface can induce aggregation of activated platelets even from low platelet concentrations, DSPC (49 mol %), cholesterol (45 mol %), DSPE-PEG (2.5 or 5 mol %), and DSPE-PEG-Biotin (1 mol %), was combined with or without DSPE-PEG-cRGD (2.5 mol %), to form cRGD-modified or unmodified biotinylated liposomal constructs. These non-fluorescent cRGD-modified or unmodified biotinylated liposomes were incubated with the avidin-coated glass coverslips for 1 hour and subsequently washed with PBS to remove any loosely-bound liposomes. This produced coverslips with a stable coating of cRGD-modified or unmodified liposomal constructs, as shown in the schematic of coverslips in the left columns of FIG. 8. LPC was obtained as described previously and incubated with the construct-coated coverslips for 1 hr in the absence or in presence of platelet agonist ADP, under gentle agitation. Post-incubation, the coverslips were gently washed with PBS to remove loosely-bound platelets from the construct-coated surface. Subsequently, the coverslips were stained with mouse anti-human Alexa Fluor® 647-anti-CD62P (red fluorescence, λmax~570 nm) that labels P-selectin on activated platelets. These stained coverslips were mounted onto glass slides and the fluorescence of active platelets aggregated onto the coverslips was imaged using inverted fluorescence microscopy. The working hypothesis behind these experiments was that coverslips coated with cRGD-modified liposomal constructs would induce GPIIb-IIIa-binding mediated enhanced aggregation of ADP-activated platelets, compared to the controls. In the absence of cRGD-modification on liposomes (unmodified liposome coating), a percentage of ADP-activated platelets may still undergo some clustering mediated by the fibrinogen present in the plasma of LPC suspension, but these platelet clusters will only aggregate minimally on the unmodified liposome surface since bare or PEGylated phospholipids (liposome membrane component) are known to prevent platelet adhesion and arrest24. Platelet aggregation was quantified as the percentage of coverslip surface area covered by platelet fluorescence. All statistical analysis was performed using ANOVA and significance was considered as $p<0.05$.

In-Vitro Evaluation of Functionally Integrated Liposomal Constructs

Figure 9:
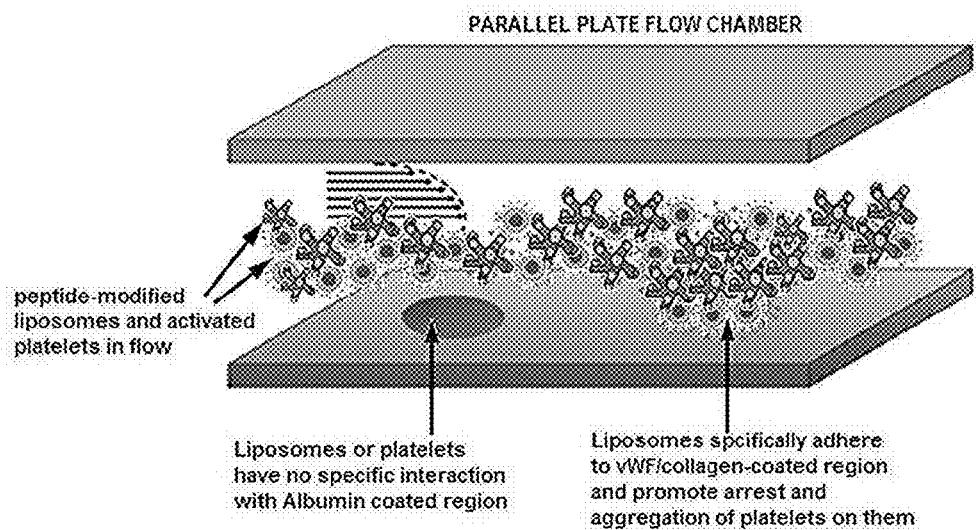

For developing functionally integrated liposomal constructs where the platelet-mimetic 'matrixadhesion' and 'aggregation' properties are combined on a single particle platform, DSPE-PEGVBP (1.25 mol %), DSPE-PEG-CBP (1.25 mol %), and DSPE-PEG-cRGD (2.5 mol %) were combined with DSPC (49 mol %), cholesterol (45 mol %), and DSPE-PEG-Fluorescein (1 mol %). Negative control liposomal constructs did not contain any lipid-peptide conjugate in their formulations, but instead contained 5 mol % of DSPE-PEG. Comparison liposomal formulations contained only 'adhesion' functionality (1.25 mol % DSPE-PEG-VBP and 1.25 mol % DSPEPEG-CMP together with 2.5 mol % DSPE-PEG, 49 mol % DSPC, 45 mol % cholesterol and 1 mol % DSPE-Fluorescein) or only 'aggregatory' functionality (2.5 mol % DSPE-PEG-cRGD together with 2.5 mol % DSPE-PEG, 49 mol % DSPC, 45 mol % cholesterol and 1 mol % DSPEFluorescein). For the experiments, glass slides were coated with adjacent circular regions of albumin (control surface with no specific adhesive interaction with any liposome formulation) and 50:50 vWF:collagen (vascular injury site mimicking protein surface with adhesive interaction with VBP- and CBP-decorated liposomes). The coated glass slides were vacuum sealed within the PPFC chamber, with the coated sides exposed to the flow (schematic shown in FIG. 9). Platelets in LPC were pre-incubated with ADP and pre-stained with red fluorescent AlexaFluor anti-CD62P. These LPC suspensions were allowed to flow through the PPFC along with various formulations of green fluorescent liposomes (unmodified, only adhesive peptide modified, only aggregatory peptide-modified or functionally integrated ones modified by all peptides), over the coated glass slides. The flow was maintained to produce wall shear stresses of 5-55 dynes/cm$^2$ for 30 minutes in a closed loop circulation. After 30 minutes, flow of just PBS was maintained for an additional 15 minutes in an open loop to remove any loosely bound constructs and platelets. The working hypothesis for this experimental design was that, liposomal constructs bearing all three peptides (VBP, CBP and cRGD) will be able to stably adhere to the vWF/collagen surface under low-to-high shear flow, recruit activated platelets in flow and promote aggregation of the activated platelets onto them at sites of liposome adhesion. Liposomal constructs bearing only 'adhesive' peptides (VBP and CBP only) or only 'aggregatory' peptide (cRGD only) will have much reduced capability of demonstrating platelet mimetic dual functions of promoting adhesion and arrest/aggregation of active platelets from flowing LPC suspensions. The slides were imaged at various time points (5, 15, 30, and 45 mins) of flow, using an inverted fluorescence microscope. For each image, liposome fluorescence (green) and activated platelet fluorescence (red) intensity were quantified using the Axiovision software. The co-localization of these two fluorescence colors was considered as a quantitative measure of liposomes adhering to the vWF/collagen surface under flow and then promoting arrest and aggregation of activated platelets onto themselves. This co-localization is qualitatively shown in pseudocolored yellow overlay in the results. The co-localization was quantified using Axiovision software, by acquiring the percentage of green pixels that also had red pixels superposed on them (at fixed pixel size) for every image and multiplying this percentage with the pixel-averaged green fluorescence intensity for that specific image. All statistical analyses were performed using ANOVA and significance was considered at $p<0.05$.

Results

Figure 8:
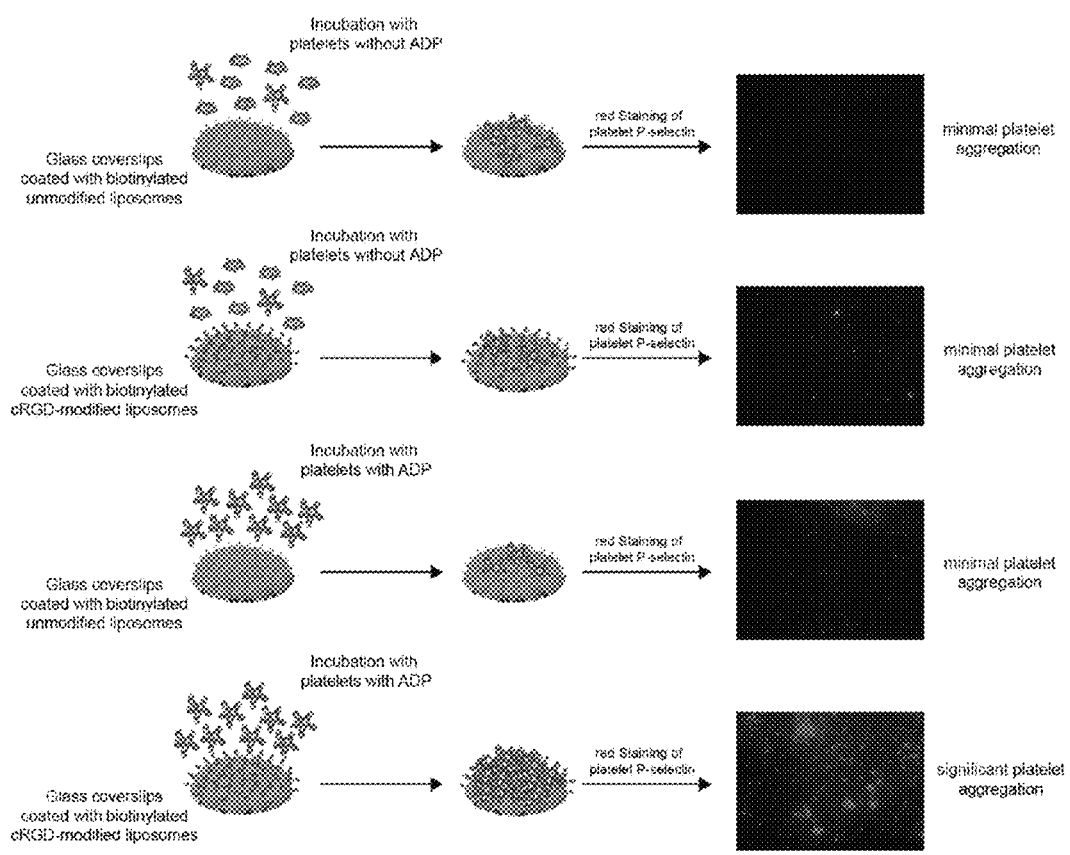
Figure 10:
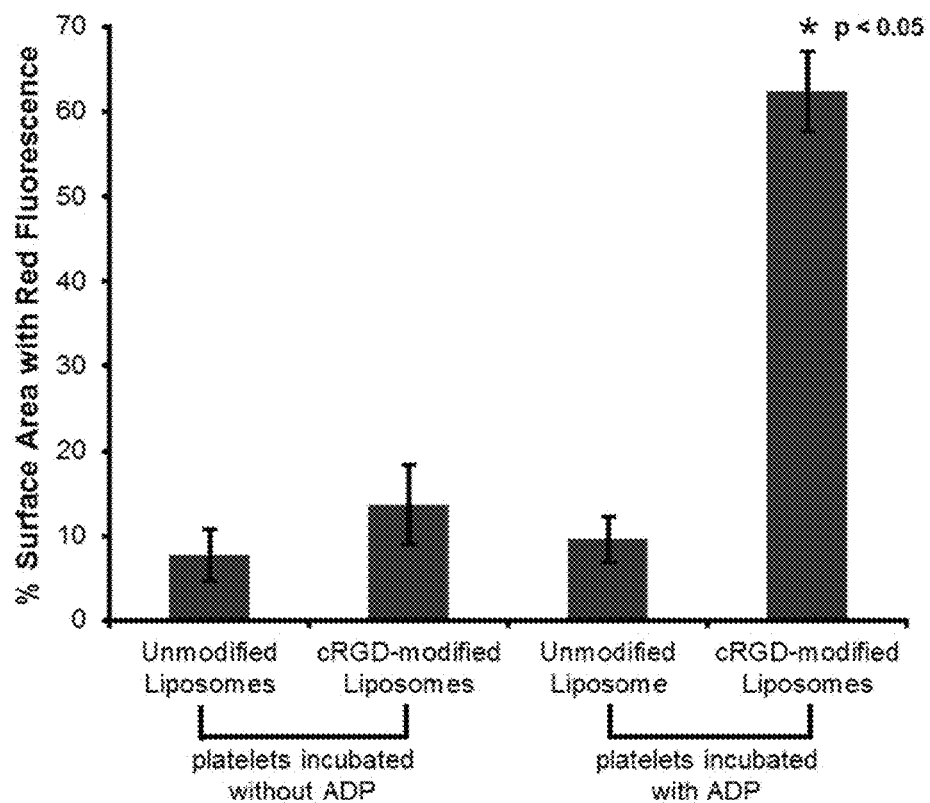
Figure 11:
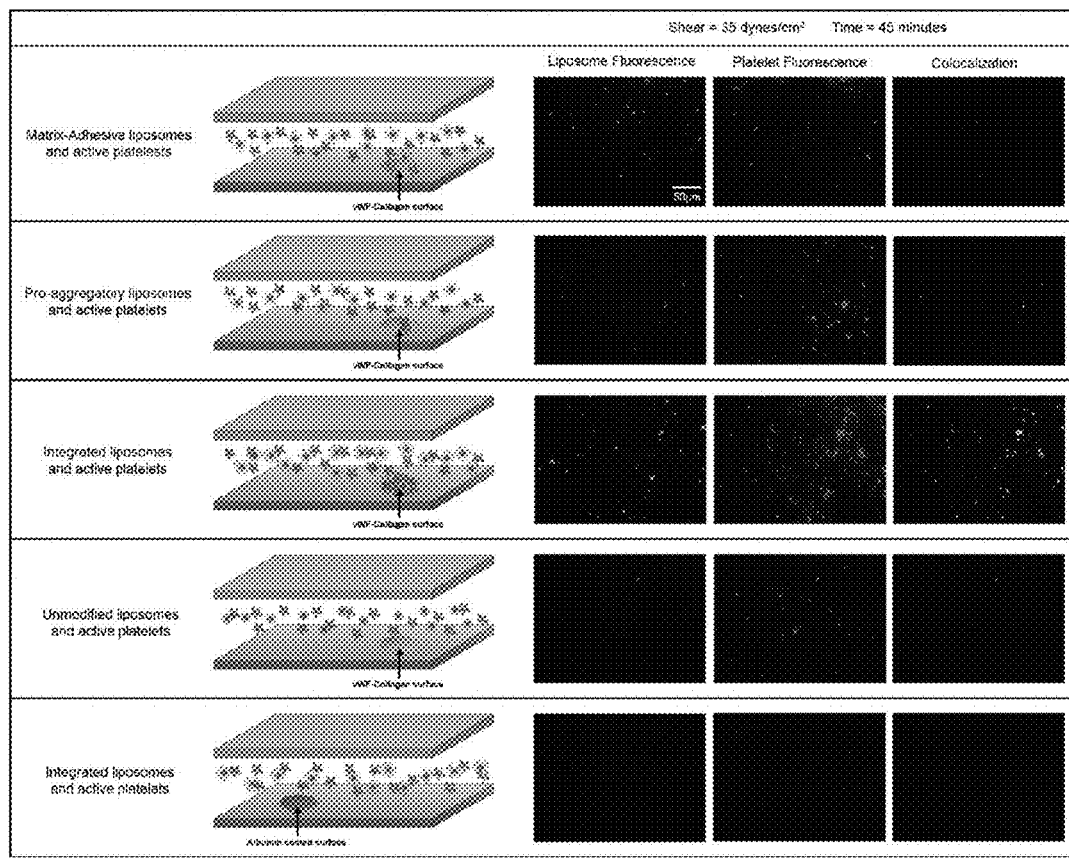
Figures 12A, 12B, 12C:
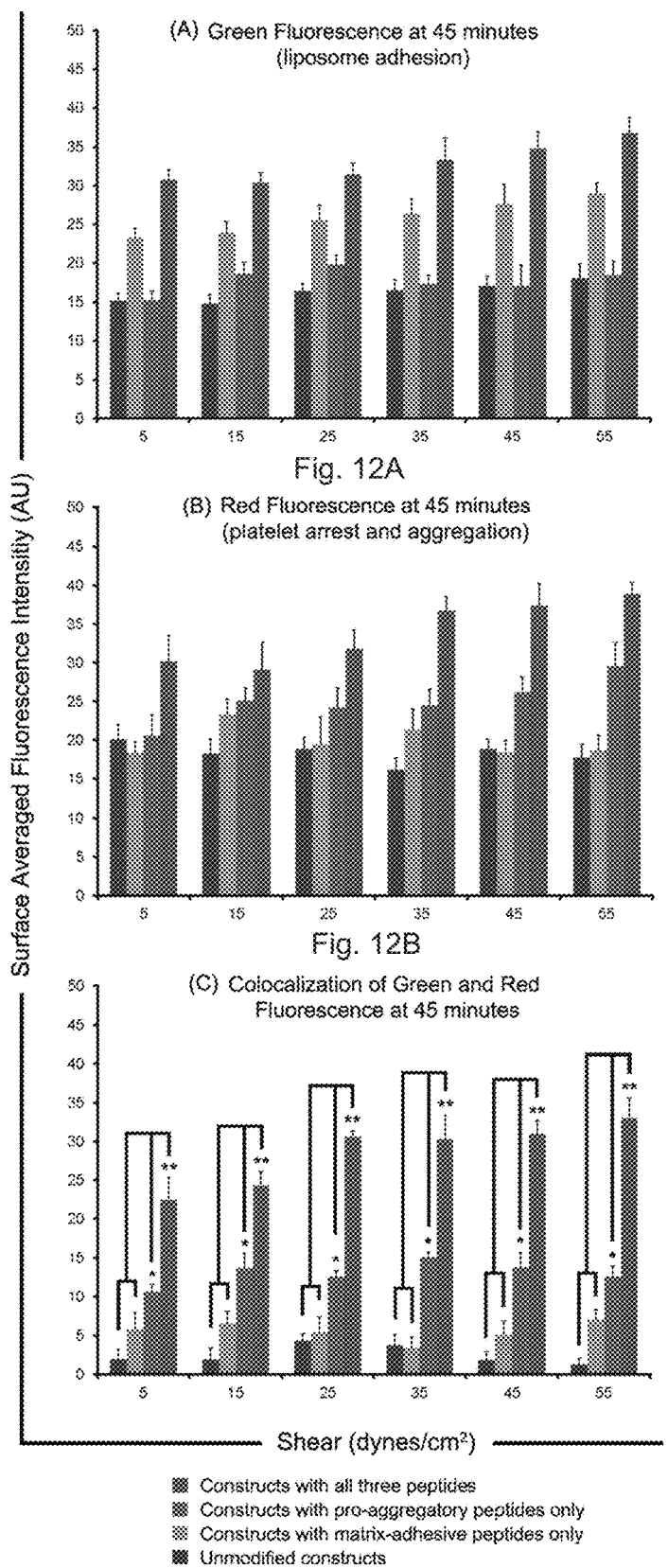

Platelet Aggregation on Biotinylated cRGD-Modified Liposomes Coated on Avidin Surfaces The last column in FIG. 8 shows representative fluorescence images for platelet interaction with the coverslip-coated various liposome formulations in absence or presence of ADP-induced platelet activation. FIG. 10 shows the corresponding quantitative data from these studies. The images and the data indicate that in absence of ADP-induced activation, quiescent platelets hardly undergo any interaction with the liposome layer, irrespective of whether the liposomes were unmodified or cRGD-modified. This also suggests that the liposomes themselves, whether unmodified or cRGD-modified, do not themselves activate (and hence aggregate) quiescent platelets. In contrast, upon ADP-induced activation, platelets undergo significantly enhanced interaction with the cRGD-modified liposomes coated on the coverslip surface, resulting in high extent of platelet aggregation. The unmodified liposomes, in comparison, show only minimal aggregation of activated platelets onto them. This establishes that the cRGD-modified liposomal constructs adhered onto a surface are capable of promoting recruitment and aggregation of activated platelets onto them. Evaluation of Functionally Integrated Liposomal Constructs in Promoting Arrest and Aggregation of Platelets on vWF/Collagen Surface Under Flow FIG. 11 shows representative set of fluorescence images and FIG. 12 shows the quantitative data from the PPFC studies evaluating the various liposomal constructs interacting with activated platelets while flowing over vWF/collagen-coated or albumin-coated surface in the PPFC set-up. In the images, the green fluorescence represents adhered liposomal constructs, the red fluorescence represents arrested and aggregated active platelets, and the yellow pseudocolor represents co-localization of the green liposomes and red fluorescent platelets in the same field of view on the vWF/collagen surface. As evident from the images in the fifth row of FIG. 11, the albumin surface hardly showed any adhesion of liposomes or arrest of platelets, and consequently the quantitative values of liposome or platelet fluorescence (and colocalization) from the albumin surfaces are not included in the quantitative data in FIG. 12. Although images were taken at six shear values between 5-55 dynes/cm$^2$ and at four time points between (5, 15, 30 and 45 min), representative fluorescent images are only shown at one shear value (35 dynes/cm$^2$) and one final time point (45 min) for convenience. The quantitative data in FIG. 12 is shown for this 45 min time point across all shear stress values studied.

From the images in FIG. 11 it is evident that liposomes bearing only aggregation promoting cRGD peptides are unable to undergo significant adhesion to the vWF/collagen surface and promote aggregation of activated platelets from the LPC condition onto them, even if they may cluster some active platelets in flow. This is suggested by the minimal green fluorescence and minimal yellow co-localization shown in the second row of images. The red fluorescence shown in this row indicates a certain extent of platelet arrest and aggregation and this is possibly due to the direct interaction of active platelets with the vWF/collagen surface and not mediated by liposomes. On the other hand, constructs bearing only adhesion promoting peptides (VBP and CBP) but no cRGD, can adhere stably to vWF/collagen surface under flow, but are unable to promote significant arrest and aggregation of activated platelets onto them from the flowing LPC suspension. This is suggested by the presence of considerable green fluorescence but minimal yellow co-localization in the first row of images. As before, the red fluorescence shown in this row does indicate a certain extent of platelet arrest and aggregation due to the direct interaction of active platelets with the vWF/collagen surface and not mediated by liposomes. Unmodified liposomes (no peptide modification) show insignificant adhesion to vWF/collagen surface (minimal green fluorescence) and consequently does not promote any arrest and aggregation of active platelets (minimal yellow fluorescence), as shown in the fourth row of images. As before, some platelet fluorescence (red) is seen here on the vWF/collagen surface due to direct interaction and arrest of active platelets on this surface. In contrast to these, functionally integrated liposomal constructs bearing all three peptides (VBP, CBP and cRGD) show high extent of green fluorescence, as well as, red fluorescence, with significant yellow overlay suggesting co-localization of the green fluorescent liposomes and the red fluorescent platelets on the vWF/collagen surface (third row of images in FIG. 11). This indicates the enhanced ability of these functionally integrated constructs to undergo stable adhesion to the vWF/collagen surface under flow and promote arrest and aggregation of activated platelets onto them, mimicking the primary hemostatic action of natural platelets.

The qualitative results indicated by the fluorescence images are further validated by the quantitative data analysis for liposome fluorescence, platelet fluorescence and co-localized fluorescence intensity shown in separate graphs in FIG. 12. From the graphs it is evident that the functionally integrated liposomes have significantly enhanced ability to adhere to the vWF/collagen surface and promote arrest and aggregation of activated platelets onto them (blue bars in the co-localization graph), compared to unmodified, pro-aggregatory or matrix-adhesive liposomes. The pro-aggregatory liposomes (modified by cRGD only) seemed to cause statistically higher aggregation compared to the unmodified and the matrix-adhesive liposomes (green bars compared to the brown and red bars in the co-localization graph), but this is probably an effect of the cRGD-modified liposomes causing clustering of active platelets in free flow and some of the heavier clusters migrating down and sticking to the vWF/collagen surface. However, this effect of pro-aggregatory liposomes is still statistically lower than the action of the functionally integrated liposomal constructs. These results establish that combining the platelet-mimetic key hemostatic functionalities of adhesion-promotion and aggregation-promotion on a single particle platform can lead to a more refined design of a synthetic hemostat.

In the native mechanism of platelet-mediated primary hemostasis in vascular injury, initially platelets adhere to injury site vWF via interaction between GPIbα of platelet surface receptor complex GPIb-IX-V. This adhesion is enhanced with increasing shear as vWF can multimerize under high shear, allowing larger extent of GPIbα interaction. The GPIbα-vWF interaction is supplemented by additional binding interaction of platelet surface receptors GPVI and GPIa/IIa to fibrillar collagen that secures the 'rolling' vWF-adhered platelets and arrests them at the injury site. In our design these two mechanisms of platelet adhesion is mimicked by decoration of multiple copies of VBP and CBP on the liposome surface. Furthermore, in natural hemostasis, the arrested adhered platelets get activated and act as nucleation points for recruitment and aggregation of more active platelets via interaction between native ligand fibrinogen with the surface integrin GPIIb-IIIa on active platelets. In our design, to mimic and amplify this process the liposome surface was decorated by multiple copies of fibrinogen-mimetic cRGD peptides, which have high affinity and selectivity to active platelet GPIIb-IIIa. The results from in vitro PPFC studies with 'functionally integrated' liposomal constructs establish successful platelet-mimicry of our design. Although in our experiments the various peptides were presented on a liposome surface, they can be potentially conjugated to any other particle platform if needed. Also, in the experiments reported here, the total mol % of peptides on the liposome surface was kept at 5 mol % while maintaining the VBP:CBP:cRGD ratio at 1:1:2. This is an initial metric of peptide decoration composition to demonstrate the feasibility of our platelet-mimetic design approach.

Example 3

In this Example, we further describe a 'synthetic platelet' technology (SynthoPlate), whose design is based on mimicking platelets' primary hemostasis mechanisms of injury site-specific adhesion (to collagen and von Willebrand factor [VWF]) and aggregation (via fibrinogen [Fg]-mediated bridging of integrin glycoprotein [GP] IIb-IIIa on activated platelets). Integration of these platelet-mimetic dual functionalities was achieved via heteromultivalent surface decoration of biocompatible lipid vesicles with VWF-binding peptide (VBP), collagenbinding peptide (CBP), and active GPIIb-IIIa-binding Fg-mimetic peptide (FMP) (FIG. 13). We have previously shown that this integrative design results in superior hemostatic performance than 'adhesion-only' and 'aggregation-only' designs. Also, in platelets' hemostatic action, colocalization of coagulation factors on the surfaces of activated procoagulant platelets at the bleeding site results in amplification of thrombin and fibrin generation (secondary hemostasis). Thus, we hypothesized that SynthoPlate-mediated direct enhancement of platelet recruitment and aggregation at an injury site would, in effect, also enhance secondary hemostatic output at that site. Therefore, we focused here on characterizing the capabilities of SynthoPlate vesicles regarding primary and secondary hemostatic mechanisms in vitro, and subsequently evaluated the systemic safety and hemostatic efficacy of SynthoPlate in vivo in a mouse model of thrombocytopenia.

Materials and Methods

Materials 1,2-Distearoyl-sn-glycero-3-phosphocholine (DSPC), carboxypoly(ethylene glycol)-modified 1,2-Distearoyl-sn-glycero-3-phosphoethanolamine (DSPE-PEG2000-COOH) and Rhodamine B (RhB)-dihexadecanoyl-sn-glycero-3-phosphoethanolamine (DHPE-RhB) were from Avanti Polar Lipids (Alabaster, Ala., USA). The peptides TRYLRIH-PQSWVHQI (VBP), [GPO]7 (CBP) and cyclo-CNPRGDY (OEt)RC (FMP) were custom-synthesized by Genscript (Piscataway, N.J., USA), conjugated to DSPE-PEG2000-COOH, and characterized by mass spectrometry. Phosphate-buffered saline (PBS), bovine serum albumin (BSA), sodium bicarbonate and fluorescent human Fg (Alexa Fluor-647-labeled) were from Thermo Fisher (Waltham, Mass., USA). Cholesterol and rat tail type I collagen were from Sigma-Aldrich (Saint Louis, Mo., USA), ADP was from Bio/Data Corporation (Horsham, Pa., USA) and human VWF (FXIII-free) was from Hematologic Technologies (Essex Junction, Vt., USA). Citrated human whole blood was obtained from freshly donated stock from healthy donors at Case School of Medicine. The parallel-plate flow chamber (PPFC) system was from Glycotech (Gaithersburg, Md., USA). For mouse studies, MOPC-21, anti-CD41 and anti-CD42 antibodies were from Abcam (Cambridge, Mass., USA). For immunostaining, rat anti-mouse CD41 antibodies were from Bio-Rad (Hercules, Calif., USA), fluorescein isothiocyanate (FITC)-labeled don-key-anti-rat IgG was from Thermo Fisher, rat anti-mouse CD31 was from Biolegend (San Diego, Calif., USA) and goat anti-rat Alexa Fluor-633-IgG was from Thermo Fisher. For immunoblot studies, lysis buffer (RIPA) was from Sigma-Aldrich, protease inhibitors were from Roche Applied Science (Madison, Wis., USA), phosphatase inhibitors and aprotinin were from Sigma-Aldrich, corn trypsin inhibitor was from Hematologic Technologies, the Protein DC assay was from Bio-Rad, rabbit polyclonal Fg/fibrin antibody was from Life Span Biosciences (Seattle, Wash., USA), horseradish peroxidase (HRP)-conjugated secondary antibody was from Cell Signaling (Danvers, Mass., USA), super signal west Pico chemiluminescent substrate was from Thermo Fisher, and antibodies against b-actin were from Santa Cruz Biotechnology (Santa Cruz, Calif., USA). All in vivo studies were carried out as per approved Institutional Animal Care and Use Committee protocols at Cleveland Clinic and the University of Pittsburgh.

Manufacture of Synthoplate

Figure 13A:
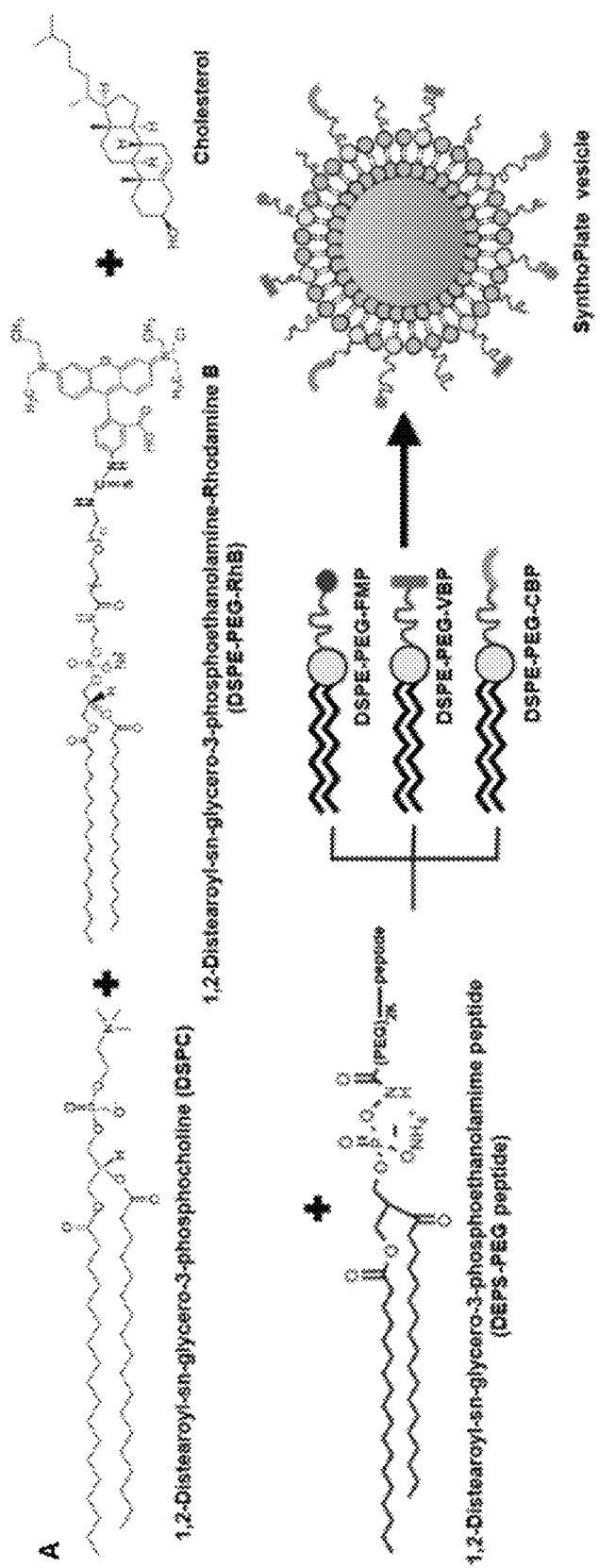
Figure 13B:
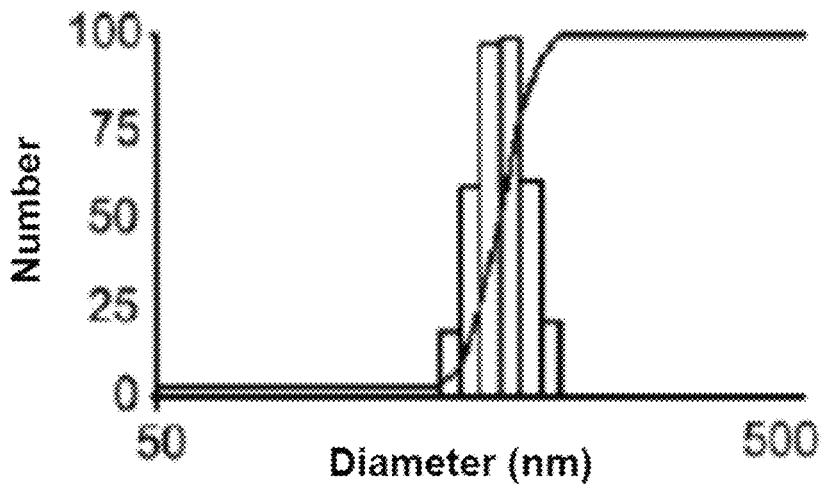
Figure 13C:
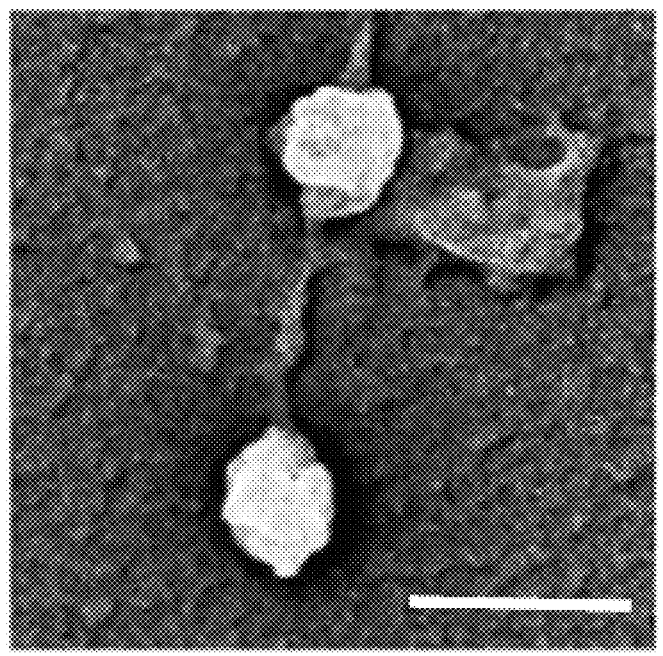

The SynthoPlate design utilizes a clinically relevant poly (ethylene glycol)-modified lipid vesicle platform, refined by heteromultivalent ligand decoration. For this, DSPC, cholesterol, DSPE-PEG-VBP, DSPE-PEG-CBP and DSPE-PEG-FMP were homogenously mixed at mole fractions of 0.50, 0.45, 0.0125, 0.0125 and 0.025, respectively, in 1:1 methanol/chloroform, and this lipid mixture was subjected to reverse-phase evaporation, PBS-based hydration, and subsequent extrusion through a 200-nm-pore membrane (Northern Lipids, Burnaby. BC, Canada) to yield heteromultivalently surface-decorated SynthoPlate vesicles (a schematic is shown in FIG. 13A). Dynamic light scattering, scanning electron microscopy and cryo-transmission electron microscopy characterization indicated vesicles~150 nm in diameter (FIGS. 13B-D). On the basis of these parameters, the theoretical ligand density per vesicle is ~50 000. By use of a Malvern zetasizer, the zeta potential of Syntho-Plate was found to be ~24.9±8.00 mV, and that for control (unmodified) particles was found to be ~25.2±9.77 mV.

In Vitro Studies of the SynthoPlate Effect on Platelet Aggregation

Turbidimetric experiments were carried out on platelet-rich plasma (PRP) with ADP as agonist, or on washed platelets (Pits) with collagen as agonist, by use of a Chronolog Aggregometer (Chrono-log, Havertown, Pa., USA), to test the interaction of SynthoPlate with active versus resting platelets. Wild-type C57Bl-6 mice were anesthetized, and whole blood was drawn by venipuncture with 0.109 M sodium citrate. Modified Tyrode's buffer (0.7 v/v) was added, and PRP was separated by centrifugation (150×g, 20 min). The platelet concentration in PRP was adjusted to 2.50×10$^8$ mL-1 with platelet-poor plasma (PPP). To prepare washed platelets, PRP was further centrifuged at 650×g for 6 min in the presence of 0.5 µM prostaglandin E$_1$ (PGE1). The resultant platelet pellet was resuspended in PBS containing 0.109 M sodium citrate (9:1, v/v) and 0.5 µM PGE1, repelleted, and resuspended in PBS to a concentration of 2.50×10 mL$^{-1}$. Aggregometry studies were conducted at 37° C. with stirring at 1200 r.p.m. ADP-mediated aggregation was performed with 400 µL of PRP (labeled as 100% PRP in FIG. 14A), or PRP diluted 50% (v/v) with either PPP (50% PRP in FIG. 14A) or PPP containing SynthoPlate or PPP containing control particles with a particle concentration of 5.00×10$^{10}$ mL$^{-1}$. To further ensure that the effect of SynthoPlate (or control particles) was specifically on platelets, collagen-based aggregation studies were performed with washed platelets instead of PRP (labeled as 100% Pits or 50% Pits in FIG. 14B), and here particles were suspended in PBS instead of PPP. Aggregation was monitored with the addition of a final concentration of 1 mM Ca$^{2+}$/Mg$^{2+}$ and with or without the addition of platelet agonists (ADP at 2.5 µM and collagen at 1 µg mL-1). The 50% dilution of platelets was considered to be a thrombocytopenic (TCP) condition, as rationalized from the clinical definition. The same SynthoPlate and control particles were also used to characterize the particle-mediated recruitment and aggregation of active platelets on 'VWF+collagen'-coated surfaces under flow in the PPFC, imaged under fluorescence microscopy. For this, calcein-stained (green fluorescent) platelets suspended in plasma (50 000 mL$^{-1}$) were passed over 'VWF+collagen'-coated surfaces along with RhB-labeled (red fluorescence) SynthoPlate (or control) particles, ADP (2.5 µM), and soluble VWF (10 µg mL$^{-1}$), with an adaptation of previously published methodology. The flow was maintained at shear stress of 50 dyn cm$^{-2}$ (shear rate of >3000 s$^{-1}$, assuming plasma to be a Newtonian fluid with a constant viscosity of Synthoplate™ evaluation in thrombocytopenia 3 0.015 P) to ensure a hemostatically relevant interaction of VWF with collagen. The colocalization of active platelets and particles (red) on the surfaces was imaged with a Zeiss inverted fluorescence microscope (Thornwood. N.Y., USA).

In Vitro Studies of SynthoPlate Effects on Thrombin and Fibrin Generation

Experiments were carried out to first study whether SynthoPlate vesicles themselves spontaneously generate thrombin in human plasma (i.e., assessing systemic coagulation risk). PRP was obtained from freshly drawn citrated human whole blood by centrifugation (150×g, 15 min), and PPP was obtained by further centrifugation of PRP (2500×g, 20 min). The thrombin-cleavable fluorogenic substrate (p-tosyl-Gly-Pro-Arg)$_2$-Rhodamine-110 (Thermo Fisher) at a final concentration of 0.1 mM (in Tris buffer, pH 7.4, 22° C.) was incubated in the presence of 5% v/v 0.5 M CaCl$_2$ with the groups: 'PPP only', 'PRP only', 'PPP+SynthoPlate', 'PRP+SynthoPlate', 'PPP+tissue factor', 'PRP+tissue factor', 'PRP+SynthoPlate+tissue factor', 'PRP+ADP+tissue factor', and 'PRP+ADP+SynthoPlate+tissue factor'. The particle concentration, in the applicable groups, was 5.00 91010 mL$^{-1}$. The resultant thrombin activity was monitored with a Bio-Tek (Winooski, Vt., USA) plate reader (excitation/emission at 498/521 nm) for 40 min. Next, for fibrin generation/deposition studies, the PPFC set-up was used as before, with some modifications. Glass slides precoated with 'collagen+VWF' or BSA were sealed within the PPFC, and exposed to flow of fresh 100% PRP (platelet count of 250 000 µL$^{-1}$), or 50% PRP (platelet count diluted 50% with PPP to 125 000 µL$^{-1}$), or 100% PPP and SynthoPlate (or control) particles, in the presence of fluorescent Fg (Alexa Fluor-647-Fg at 1.5 mg mL$^{-1}$ added at 3% v/v), with or without ADP. The 'control' particles had only proadhesive peptides (VBP and CBP only; no FMP) such that they can still bind to the 'VWF+collagen' substrate but cannot recruit and aggregate active platelets. The flow was maintained at 50 dyn cm$^{-2}$ for 15 min. In this set-up, SynthoPlatemediated recruitment and aggregation of active platelets on the 'VWF+collagen' surface was hypothesized to augment the availability of procoagulant active platelet membrane for facilitating secondary hemostatic mechanisms, leading to amplified generation and deposition of fibrin(ogen) during the 15-min time-window. This deposition was imaged with inverted fluorescence microscopy (emission, 665 nm). At 15 min, the flow was stopped, and the clots on the slides were incubated with streptokinase in PPP (20 µL per mL of PPP) for 60 min. The resultant lysed clots were analyzed with a fibrin D-dimer-specific spectrophotometric ELISA assay (Thermo Fisher) according to the manufacturer's instructions, and D-dimer levels were calculated from a standard calibration curve. The D-dimer analysis was to confirm that the clot fluorescence observed was indeed from fibrin generation and not just Fg.

Effects of SynthoPlate in Severely TCP Mice

Figure 16A:
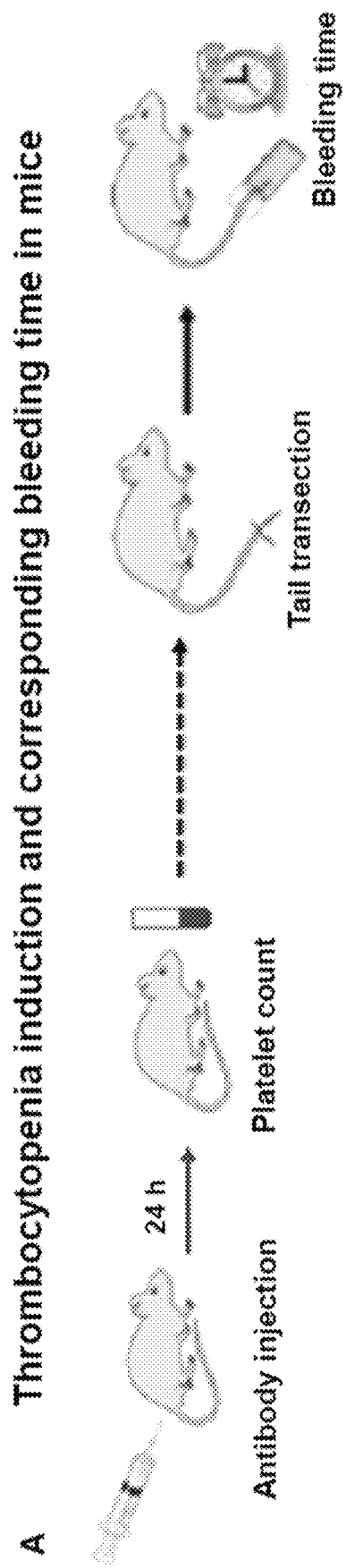

We adapted a model of passive immune thrombocytopenia in mice with platelet-specific antibodies. Wild-type C57/BL6 mice were injected intraperitoneally with a combination of anti-CD41 and anti-CD42 antibodies (1:1 ratio at 1-10 µg total) and, 24 h later, platelet counts were performed with an Advia 120 Hematology analyzer (Erlangen, Germany) (six mice per group). For bleeding time assessment, 24 h after administration of 10 µg of antibody, tails of TCP mice were transected 2 mm from the tip with a surgical blade, and immersed in 37° C. saline; the time needed for bleeding to stop was recorded (a schematic is shown in FIG. 16A). Next, similarly treated TCP mice were injected with 150 µL of various doses (100, 500 or 1000 $nL^{-1}$) of SynthoPlate or control (unmodified) particles via the jugular vein and, 2 h after particle injection, the mouse tails were transected as before to record the bleeding time. The 2-h-circulation time-period was chosen as a feasibility metric for evaluating the 'prophylactic window' of the SynthoPlate technology, and future studies will focus on expanding this window to longer circulation lifetimes. All tail-bleeding studies were performed in accordance with standardization parameters highlighted by the ISTH. After bleeding time studies, mice were killed, and 4-5-mm tail-pieces proximal to the transection site were cut, washed in PBS, fixed in paraformaldehyde for 24 h, and then cryoprotected in 30-60% sucrose and flash frozen in OCT compound (Tissue Tek, Torrance, Calif., USA). Cryoblocks were prepared in cryo-molds (Electron Microscopy Sciences, Hatfield, Pa., USA) over dry ice and 2-methylbutane, and 9-lm-thick sections were cut with a Leica CM1950 cryostat (Buffalo Grove, Ill., USA) and collected on superfrost glass slides (Thermo Fisher) for staining. For immunostaining, frozen sections were air-dried, rinsed in PBS, and blocked with 0.1% Tween-20 and 1% BSA. A sequential staining protocol was followed, in which sections were first incubated with rat anti-mouse CD41 antibodies overnight at 4° C., and then washed in PBS and incubated with an FITC-labeled donkey-anti-rat IgG for 2 h. After additional washes, sections were incubated with rat anti-mouse CD31 for 2 h, and then washed and labeled with goat anti-rat Alexa Fluor-633-IgG. Slides were mounted with Vectashield, and imaged under a Leica fluorescence microscope. In additional experiments, similar tail sections from TCP mice treated with SynthoPlate or control particles were collected directly into lysis buffer containing protease inhibitors, phosphatase inhibitors, corn trypsin inhibitor, and aprotinin. Tails were disrupted by sonication, and lysates were clarified by centrifugation at 12 000×g for 15 min at 4° C. The supernatant was collected, and protein was measured with the Protein DC assay. For immunoblotting, tail extracts were mixed with 5×SDS sample buffer containing β-mercaptoethanol, and heated at 95° C. for 5 min. Samples were resolved by 10% SDS-PAGE with 25 µg of protein in each lane, and transferred to poly(vinylidene difluoride) membranes. Membranes were probed overnight at 4° C. with a 1:5000 dilution of rabbit polyclonal Fg/fibrin antibody (Life Span Biosciences). Bound antibody was detected with an HRP-conjugated secondary antibody and super signal west Pico chemiluminescent substrate. The membrane was stripped in stripping buffer containing 15 g $L^{-1}$ glycine, 1 g $L^{-1}$ SDS, and 10 mL $L^{-1}$ Tween-20 (pH 2.2), blocked, and reprobed with antibodies against β-actin.

Assessing the Systemic Safety and Biodistribution of SynthoPlate During 2 h of Circulation For systemic safety analysis, wild-type or TCP mice were intravenously injected with SynthoPlate or control (unmodified) particles and, 2 h after particle injection, blood was collected via cardiac puncture in sodium citrate (0.109 M, 3.2%) and analyzed with an immunoturbidimetric agglutination assay for circulating fibrin D-dimer levels (STA-Liatest D-Di; Diagnostica Stago, Parsippany, N.J., USA), according to the manufacturer's instructions. In parallel experiments, mice were injected intravenously with 8 lg $kg^{-1}$ lipopolysaccharide (LPS) (positive control) or 120 µL of SynthoPlate or control particles (1000 $nL^{-1}$). At 30 min and 2 h after injection, blood was drawn from the facial vein directly into tubes © 2016 International Society on Thrombosis and Haemostasis Synthoplate™ evaluation in thrombocytopenia 5 containing sodium citrate, corn trypsin inhibitor, and aprotinin, and centrifuged at room temperature for 10 min at 850×g; the plasma was then collected and analyzed with a double-antibody sandwich ELISA for prothrombin fragment 1+2, according to the manufacturer's instructions (Biosource, San Diego, Calif., USA).

For biodistribution studies, mice were injected intravenously with SynthoPlate, and killed after 2 h with overdose of anesthesia cocktail. Various organs were harvested, rinsed in PBS, and freeze-dried to obtain the dry weight The organs were homogenized at 4000 r.p.m. (BeadBug Microtube Homogenizer; Benchmark Scientific, Edison, N.J., USA), and homogenates were shaken overnight at 750 r.p.m. and 37° C. with 1:1 methanol/chloroform solution to extract the RhB-labeled lipids. The resultant samples were centrifuged at 1000×g for 10 min, the supernatant containing RhB-labeled lipids was collected, and the fluorescence in the supernatant was determined with a Bio-Tek Plate reader (excitation, 550 nm; emission, 590 nm). The SynthoPlate percentage in various organs was determined by calculating the concentration (ng $mL^{-1}$) of particles in the supernatant from a calibration curve. In complementary studies, SynthoPlate particles were radiolabeled either by incorporating 3H-tagged cholesteryl ester in the vesicle membrane, or encapsulating indium chloride ($^{111}InCl_3$) in the vesicle core. Following tail-vein injection of these particles, mice were either killed for harvesting of organs and blood for scintillation counting of 3H-labeled particles, or wholebody imaged by single photon emission computed tomography for assessment of the $^{111}InCl_3$-labeled particle distribution.

Statistical Analysis

Where applicable, data were expressed as mean±standard deviation. Aggregometry results were analyzed by one-way ANOVA with Bonferroni post hoc testing for multiple comparisons by the use of SIGMASTAT 3.5. Thrombin and fibrin assay results were analyzed by one-way ANOVA and Tukey's test. For some in vivo results, analyses were also carried out with a two-tailed Student's t-test. A P-value of <0.05 was considered to be statistically significant.

Results

In Vitro Studies of SynthoPlate-Mediated Primary Hemostasis Mechanisms

Representative aggregometry data for PRP or washed platelets, along with corresponding histograms of percentage aggregation, are shown in FIG. 14. As is evident from FIG. 14A1, without platelet activation, SynthoPlate itself has no aggregatory effect on platelets, as the turbidimetric trace for this (brown) was same as that for resting (without ADP) platelets (indigo). This suggests that SynthoPlate will not activate resting platelets in the circulation. Upon agonist addition, platelet aggregation was observed in 100% PRP as well as in 100% platelets (green traces in FIG. 14A1, B1). This aggregation was significantly reduced when PRP was diluted by 50% v/v with PPP or platelets were diluted with saline (purple traces in FIG. 14A1,B1). This dilution effect was not rescued when control (unmodified) particles were added (red traces in FIG. 14A1,B1). In contrast, addition of SynthoPlate particles significantly rescued the aggregation (cyan traces in FIG. 14A1,2B1). Statistical analyses (FIG. 14A2,B2) clearly show this ability of SynthoPlate to improve the aggregation of diluted platelets. Also, the SynthoPlate vesicles themselves did not show any aggregation in presence of platelet agonists and $Ca^{2+}$. Fluorescence microscopy studies in PPFC demonstrated that RhB-labeled (red fluorescent) SynthoPlate particles showed significant colocalization (yellow overlay) with calcein-stained (green fluorescent) active platelets on a 'VWF+collagen' surface, whereas unmodified, 'adhesion-only' and 'aggregation-only' particles showed minimal colocalization. These results are in accordance with our previously reported findings. Altogether, these studies indicate that: (i) SynthoPlate interacts specifically with activated platelets to augment their aggregation; and (ii) this aggregation can be enhanced selectively at the site of 'VWF+collagen' exposure (amplification of primary hemostasis) via SynthoPlate action.

In Vitro Studies of SynthoPlate-Mediated Thrombin Generation

Figure 15A:
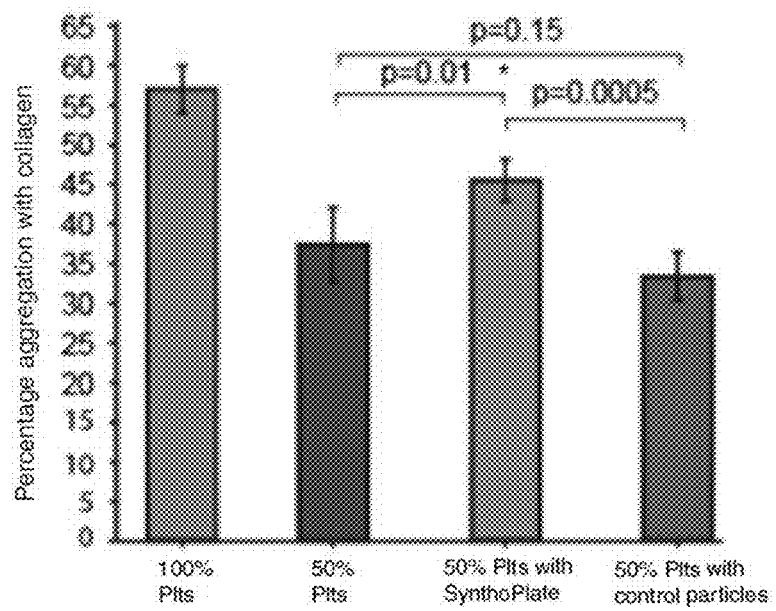
Figure 15B:
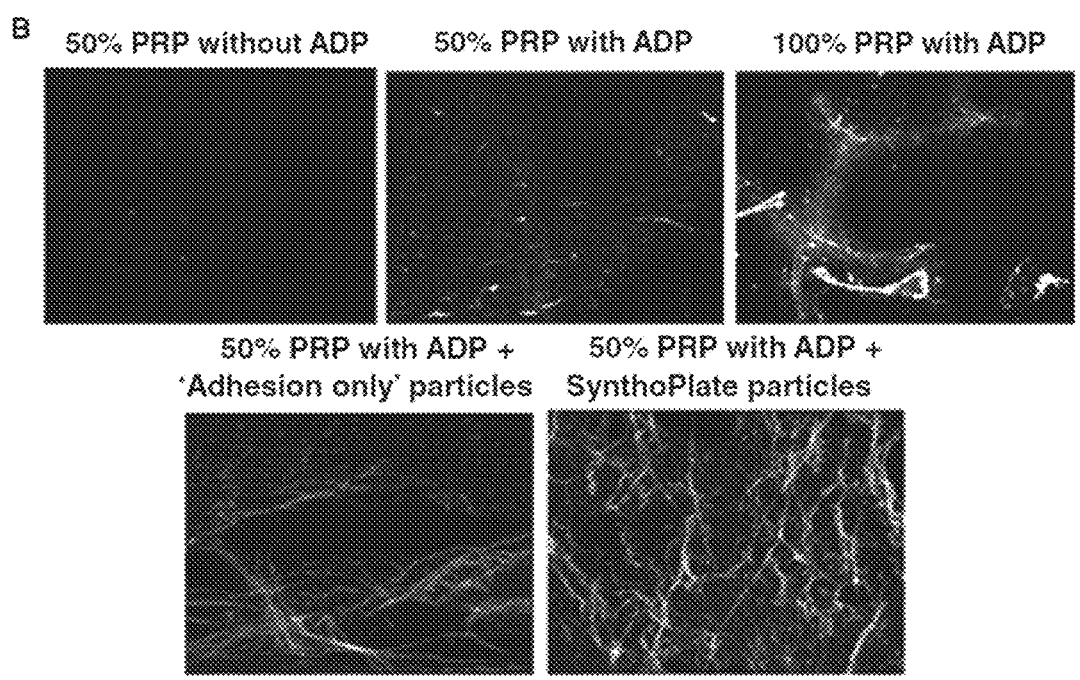
Figure 15C:
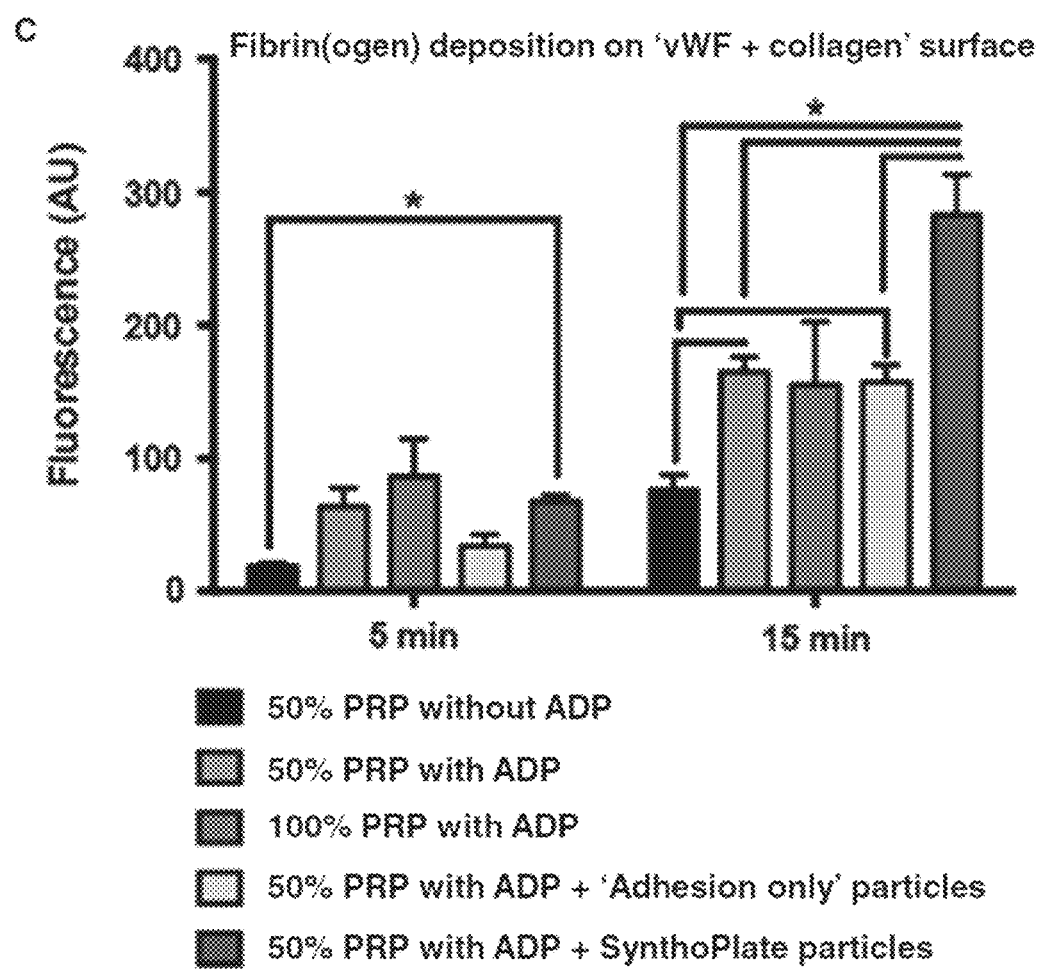
Figure 15D:
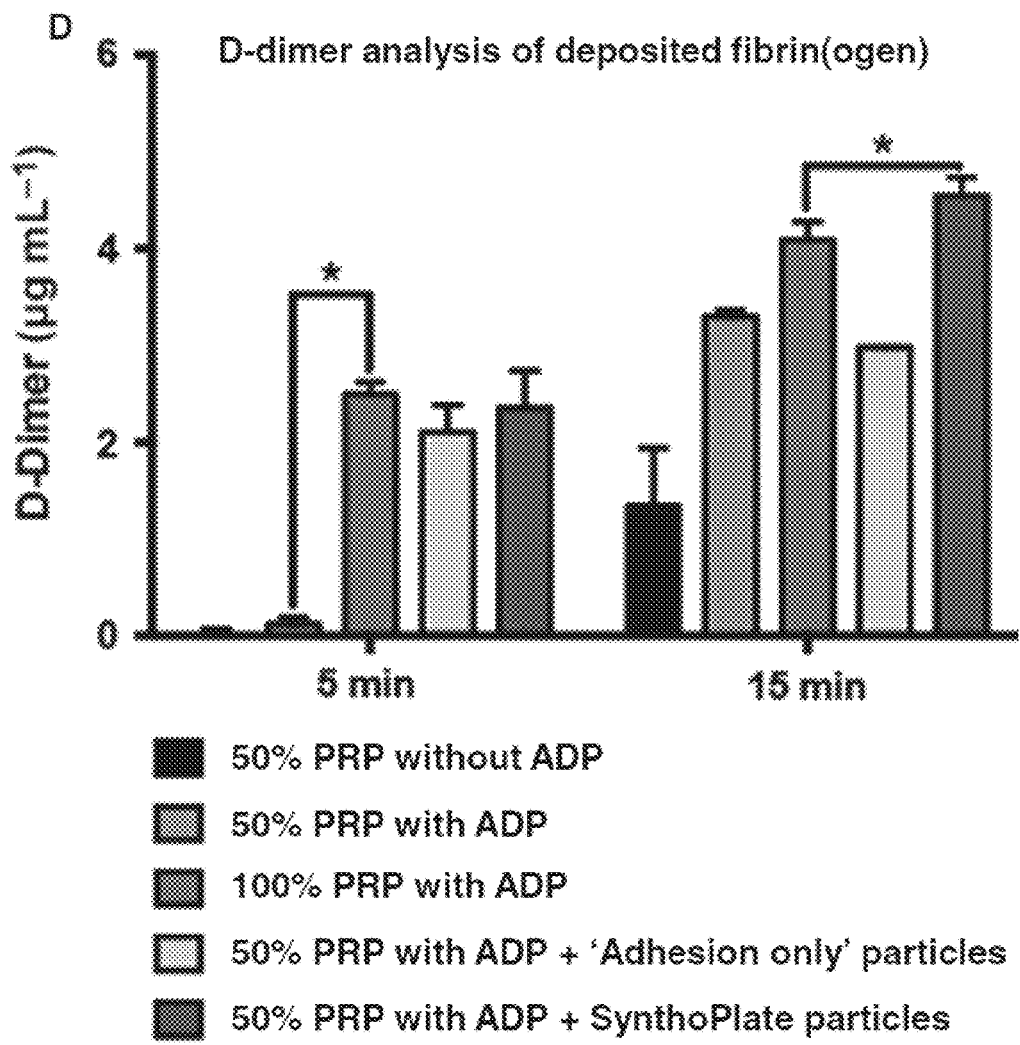

FIG. 15A shows the table for thrombin generation parameters obtained for the various groups studied. As is evident from the results, without tissue factor or platelet agonist (ADP), addition of SynthoPlate to recalcified PRP or PPP did not induce or accelerate rapid thrombin generation, and thrombin generation occurred with a much longer lag time, as is common for recalcified plasma. In the presence of tissue factor and/or ADP, thrombin generation was drastically accelerated in PRP (or PPP) even without SynthoPlate, and the reaction speed increased slightly when SynthoPlate was present. This indicates that SynthoPlate itself does not directly influence thrombin generation in plasma, but can possibly indirectly influence thrombin generation if it can recruit procoagulant active platelets at the site of injury and tissue factor exposure. This possibility was further confirmed by the results of the fibrin(ogen) generation/deposition study under flow (representative images and quantitative results are shown in FIG. 15B,C). In this case, during the 15-min time-window, the fluorescence of deposited fibrin(ogen) significantly increased when ADP-activated 50% PRP was passed with SynthoPlate over a 'VWF+collagen' surface, as compared with the control conditions. The D-dimer ELISA studies further confirmed that the deposited clot in this group contained a significant amount of fibrin (FIG. 15D). All together, these studies confirm that SynthoPlate does not have any innate ability to stimulate coagulation in plasma (and therefore has a minimum systemic procoagulant risk), but can, 'in effect', augment coagulatory output at the injury site by enhancing the recruitment and aggregation of active platelets at the site.

Figure 2:
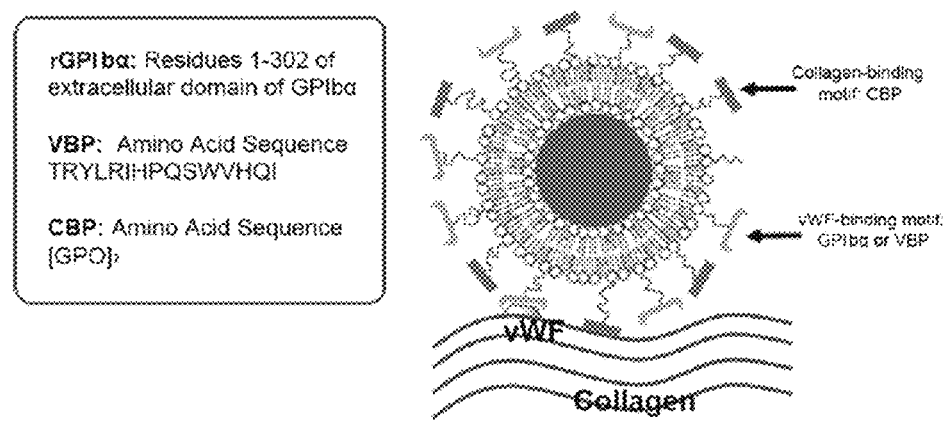
FIG. 2 is a design of heteromultivalent liposomes surface-modified with vWF-binding and collagen-binding ligand motifs that can mimic the adhesion mechanisms of platelets under flow.
Figure 16B:
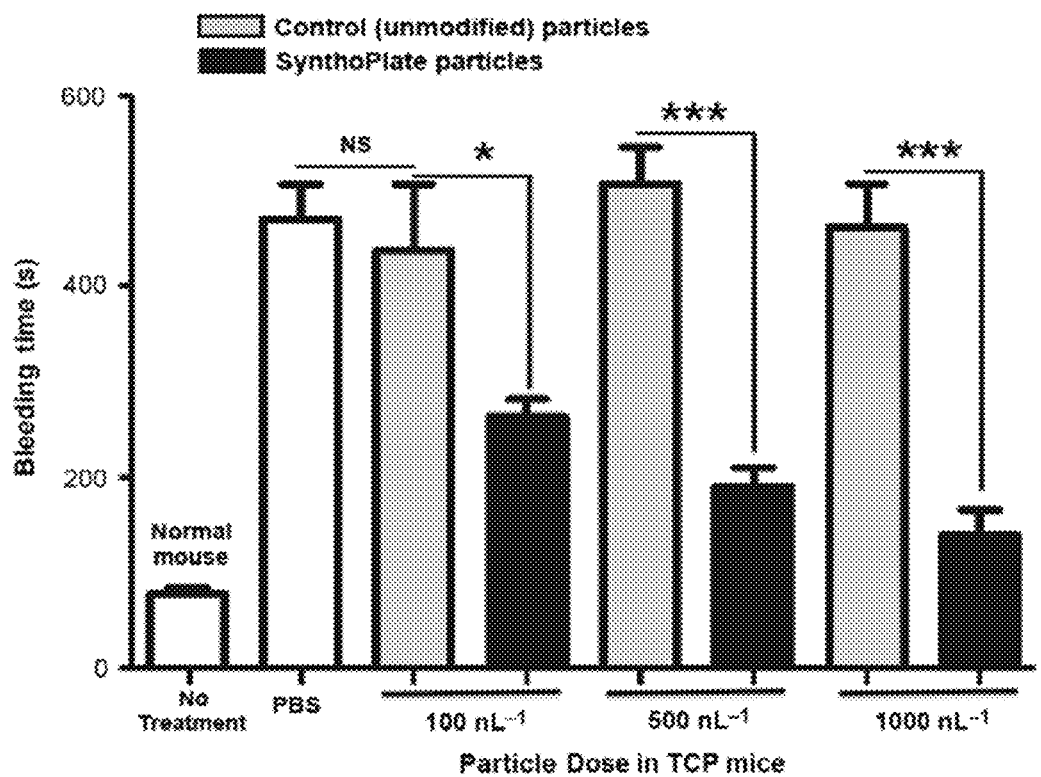
Figure 17A:
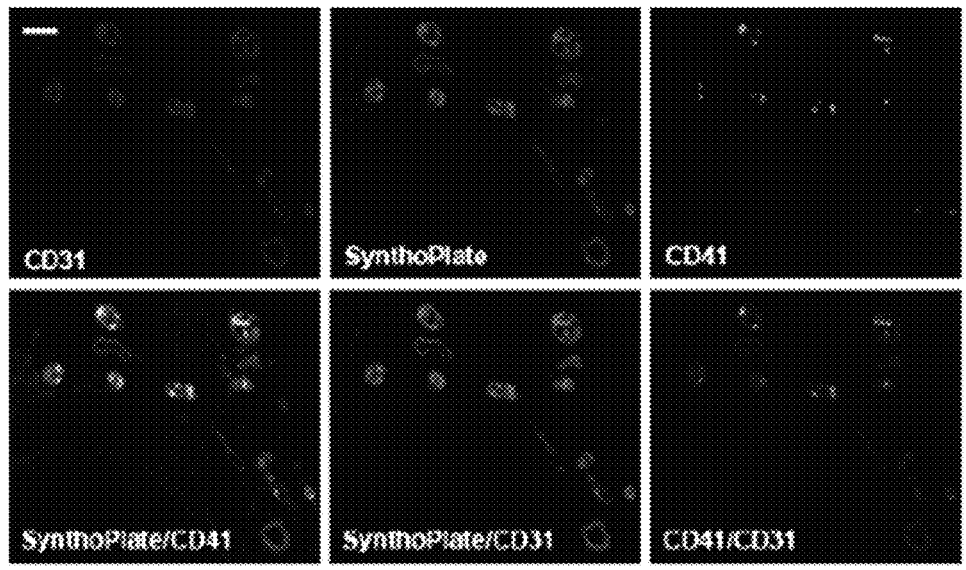
Figure 17B:
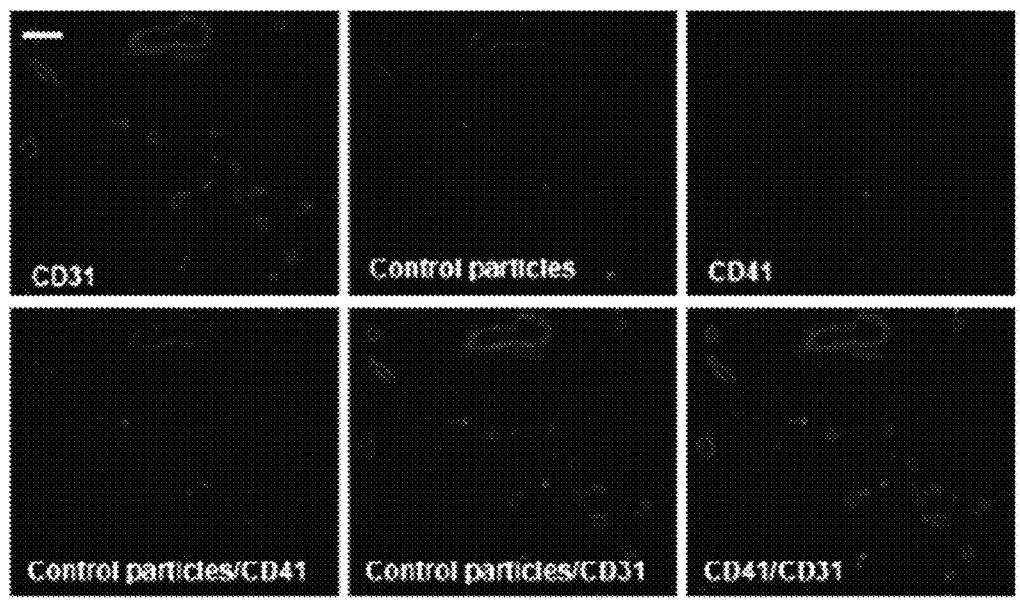
Figure 17C:
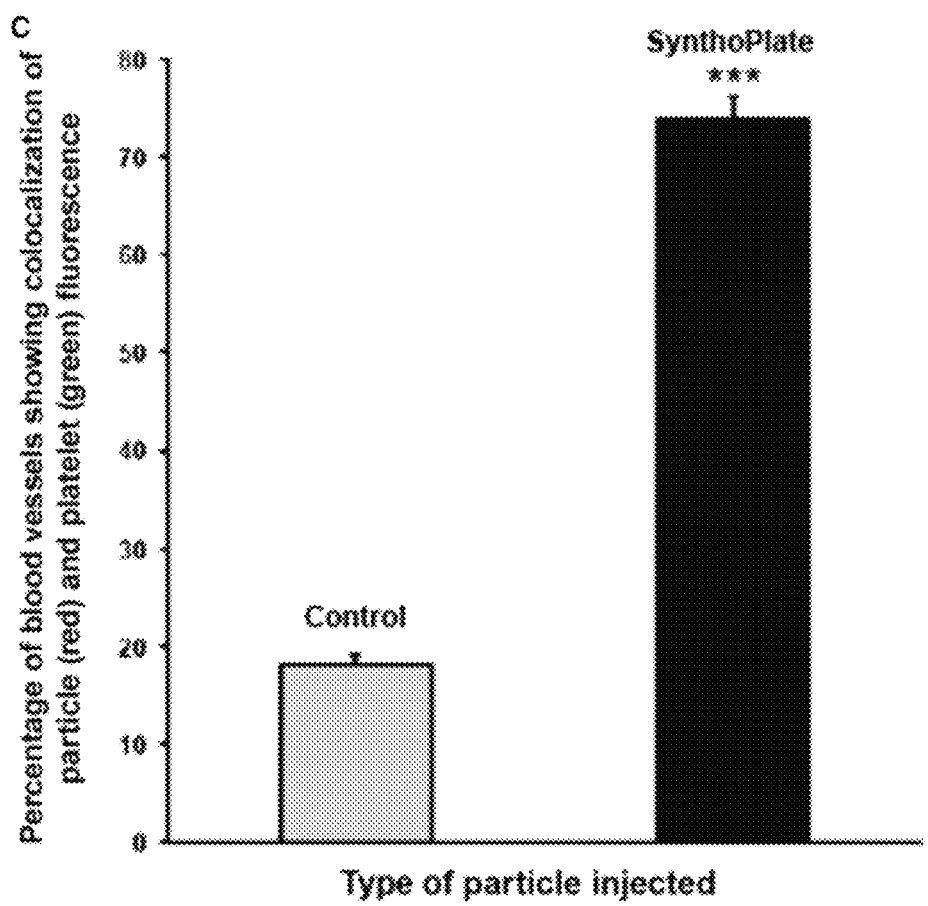
Figure 17D:
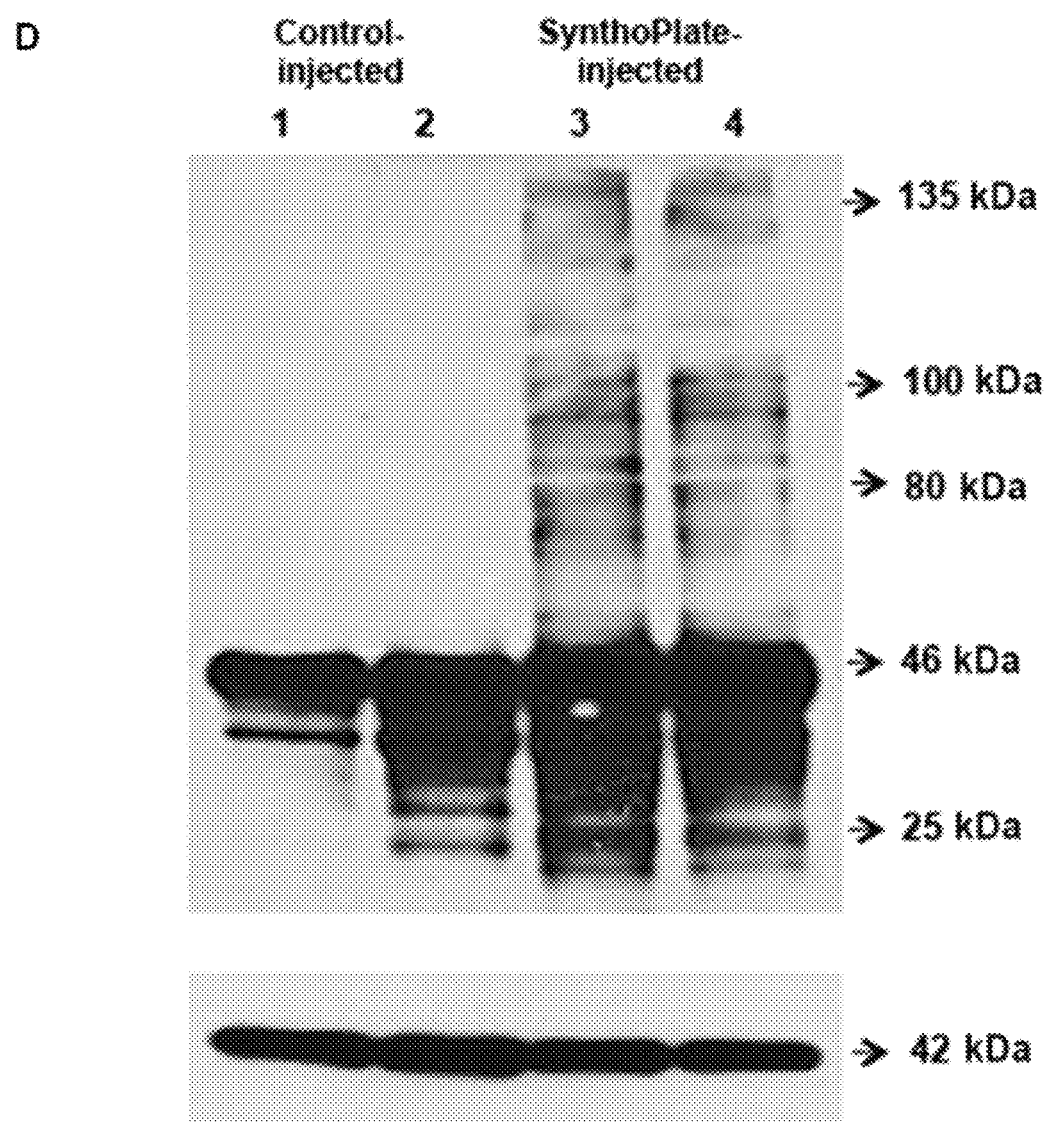

Severe Thrombocytopenia Induction in Mice and Effects of SynthoPlate on Tail Bleeding FIG. 16A1 shows the platelet count following antibody treatment, demonstrating that a total dose of 10 μg of antibody combination (5 μg each) resulted in a ~90% reduction in platelet count (severe thrombocytopenia). Injection of PBS or non-specific mouse IgG (MOPC-21) did not deplete platelets. The effect of platelet depletion on the hemostatic capacity of mice is shown in FIG. 16A2, where 10 lg of antibody injection (i.e., platelet depletion by ~90%) resulted in a four-fold to five-fold increase in tail-bleeding time. This severe thrombocytopenia condition was subsequently used to test the ability of prophylactically administered SynthoPlate to improve hemostasis. FIG. 16B shows the effect of SynthoPlate versus control particle treatment on tail-bleeding time in TCP mice. As is evident, PBS alone or control particles were unable to correct the prolonged bleeding time (400-500 s). In contrast, SynthoPlate was able to significantly correct the bleeding time in a dose-dependent manner. The highest dose of SynthoPlate (1000 $nL^{-1}$, equivalent to the murine native platelet concentration) reduced the bleeding time to ~150 s (>60% reduction as compared with controls), which is close to that of normal mice (~100 s, shown for comparison). These studies demonstrate that SynthoPlate could efficiently correct the hemostatic defect in thrombocytopenia. FIGS. 17A,B shows representative immunofluorescence images of cryosectioned tail tissue immediately proximal to the tail transection site, showing vascular endothelium (CD31 in blue), particle fluorescence (red), platelets (CD41 in green), and corresponding overlays, for SynthoPlate-treated versus control particle-treated TCP mice. FIG. 5C shows the percentage of the vasculature that demonstrated colocalization of CD41 (platelets) and SynthoPlate (or control) particles, determined from 24 representative images per injection group (six mice per group) by manual counting. These images clearly indicate that SynthoPlate has significantly greater ability than control (unmodified) particles to enhance the recruitment and aggregation of platelets in the injured vessels in TCP mice. FIG. 16D shows representative immunoblot data (for fibrin/Fg, and for β-actin as a loading control) for tail tissue from SynthoPlate-treated versus control particle-treated TCP mice. Individual Fg a, b and c chains are not well resolved, but are seen as prominent bands of ~45-63 kDa. However, higher molecular weight bands, consistent with thrombin-cleaved cross-linked fibrin, are apparent in the SynthoPlate-treated mice (lanes 3 and 4), but are not present in control particle-treated mice (lanes 1 and 2). These results further indicate that, in TCP mice, SynthoPlate-mediated platelet recruitment and aggregation at the injury site (amplification of primary hemostasis) also enhance thrombin generation and fibrin deposition at the site (secondary hemostasis) to improve overall hemostatic capability.

Systemic Safety and Biodistribution of SynthoPlate During 2 h of Circulation

Figure 18A:
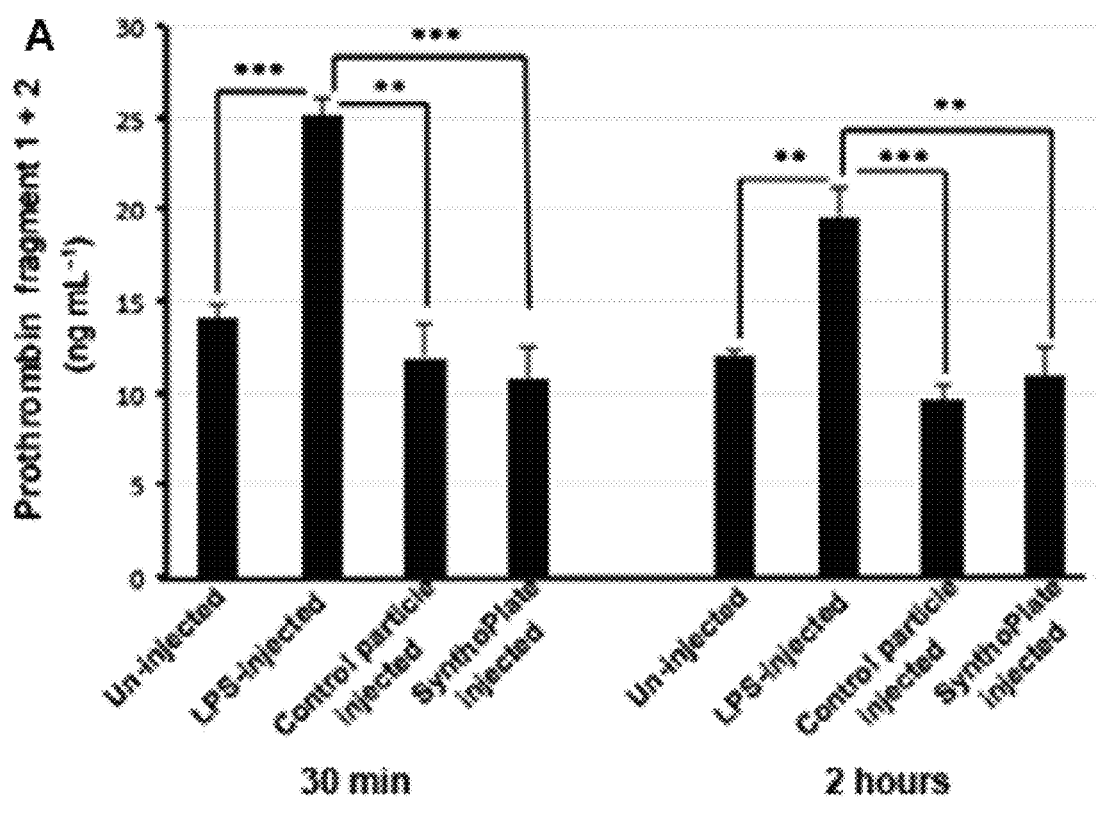
Figure 18B:
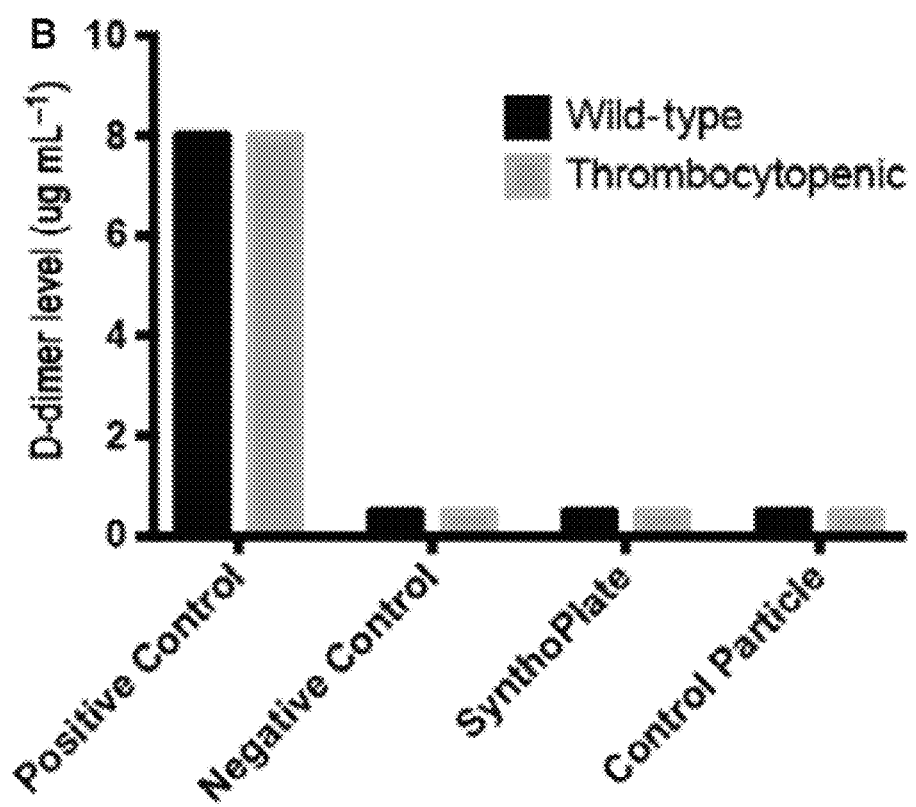
Figure 18C:
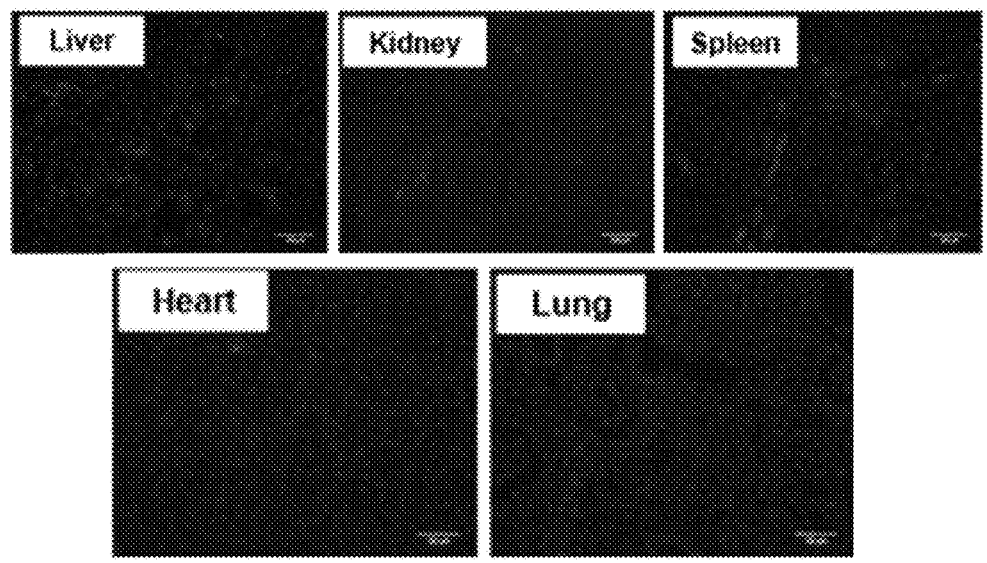
Figure 18D:
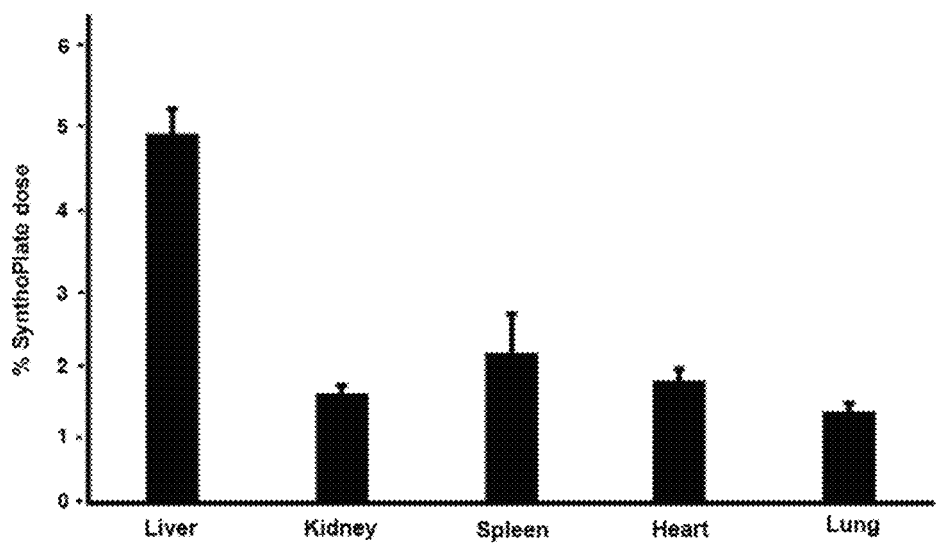

FIG. 18A shows 30-min and 2-h time-point results for ELISA-based analysis of prothrombin fragment 1+2 in SynthoPlate-injected mice (untreated mice or LPS-injected mice as controls). SynthoPlate particles did not enhance prothrombin fragment levels, indicating their minimum procoagulant activity in plasma. This was further validated by the Stago D-dimer assay results shown in FIG. 6B, where neither control nor TCP mice were found to have enhanced levels of fibrin D-dimer in the systemic circulation at the 2-h time-point following SynthoPlate or control particle administration (as compared with manufacturer-supplied controls). These in vivo results, combined with those of previous in vitro assays, further establish that SynthoPlate does not have systemic prothrombotic and procoagulant effects. FIG. 18C shows representative cryosection fluorescence images of tissues from various clearance organs harvested from killed mice at the 2-h time-point, and FIG. 18D shows the percentage localization of SynthoPlate particles (based on RhB fluorescence) analyzed from homogenates of such organs. During the 2-h circulation period, only ~15% of the injected dose was cleared, mostly in the liver and spleen, and minimally in other organs. This suggests that the majority of the dose remained in the circulation to facilitate hemostasis in the event of injury. In fact, complementary studies using radiolabeled particles further indicate that SynthoPlate has a reasonably long circulation residence time. As SynthoPlate design utilizes polyethylene glycol-decorated lipid vesicles, this long circulation capability and low clearance are in good agreement with reports for similar nanoparticles (e.g., Stealth liposomes).

In this example, we show that the SynthoPlate vesicles themselves do not have systemic prothrombotic or procoagulant risks, but can amplify activated platelet-mediated primary and secondary hemostatic mechanisms selectively at a bleeding site, even at low platelet concentrations. Our in vivo studies further confirmed that prophylactic administration of SynthoPlate can dose-dependently improve hemostasis in a tail-bleeding model in severely thrombocytopenia (TCP) mice, with higher doses being capable of correcting bleeding times to levels comparable to that of normal mice. One should note that the starting platelet count in normal mice (~1 million per microliter) is significantly higher than that in normal human (~250 000 per microliter), and hence the severity of the TCP bleeding risk in mice is associated with the percentage platelet depletion and not the absolute number of remaining platelets. Also, as tail-bleeding studies may have some experimental heterogeneity, we have meticulously followed the ISTH standardization recommendations for this model to minimize errors and variabilities. Immunofluorescence microscopy and immunoblot analyses confirmed striking colocalization of murine platelets and SynthoPlate, as well as enhanced formation of fibrin in hemostatic foci of SynthoPlate-injected mice. In vivo, SynthoPlate vesicles showed reasonably long circulation periods, and were primarily cleared by the liver and spleen. The SynthoPlate technology may also find potential uses in the emergency treatment of traumatic hemorrhage, and as a targeted drug delivery platform in various platelet-relevant diseases.

From the above description of the invention, those skilled in the art will perceive improvements, changes and modifications. Such improvements, changes, and modifications are within the skill of the art and are intended to be covered by the appended claims. All patents, patent applications, and publications cited herein are incorporated by reference in their entirety.

We claim:

1. A method of promoting hemostasis in a subject in need thereof, the method comprising:
administering to the subject a biocompatible flexible nanoparticle that includes an outer surface and a plurality of peptides conjugated to the surface, the peptides including a plurality of von Willebrand factor-binding peptides (VBPs), collagen-binding peptides (CBPs) and an active platelet GPIIb-IIIa-binding peptides (GBPs), wherein the biocompatible flexible nanoparticle promotes arrest and aggregation of active platelets onto sites of the synthetic platelet adhesion.

2. The method of claim 1, wherein the VBPs, CBPs, and GBPs can be spatially or topographically arranged on the flexible nanoparticle surface such that the VBPs, CBPs, and GBPs do not spatially mask each other.

3. The method of claim 1, wherein the VBPs, CBPs, and GBPs are conjugated to the nanoparticle surface with PEG linkers.

4. The method of claim 1, wherein the flexible nanoparticle has an about 2 to about 5 μm diameter discoidal shape and an about 10 to about 50 kPa mechanical elastic modulus.

5. The method of claim 1, the VBPs having SEQ ID NO: 1, the CBPs having SEQ ID NO: 2, and the GBPs having SEQ ID NO: 3.

6. The method of claim 1, wherein the ratio of VPBs to CBPs provided on the nanoparticle surface is about 70:30 to about 30:70.

7. The method of claim 1, wherein the ratio of VPB:CBP:GBP is about 1:1:2 to 1:2:1 to 2:1:1.

8. The method of claim 1, wherein the nanoparticle comprises a liposome.

9. The method of claim 1, wherein the nanoparticle comprises alternating layers of albumin and a polyallyamine.

10. The method of claim 1, wherein the subject has or is at risk of thrombocytopenia.

* * * * *

```
SEQUENCE LISTING

<160> NUMBER OF SEQ ID NOS: 3

<210> SEQ ID NO 1
<211> LENGTH: 15
<212> TYPE: PRT
<213> ORGANISM: Homo sapiens

<400> SEQUENCE: 1

Thr Arg Tyr Leu Arg Ile His Pro Gln Ser Trp Val His Gln Ile
1               5                   10                  15

<210> SEQ ID NO 2
<211> LENGTH: 21
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: 4HYP 4-Hydroxyproline
<220> FEATURE:
<221> NAME/KEY: MISC_FEATURE
<222> LOCATION: (6)..(6)
<223> OTHER INFORMATION: 4HYP 4-Hydroxyproline
<220> FEATURE:
<221> NAME/KEY: MISC_FEATURE
<222> LOCATION: (9)..(9)
<223> OTHER INFORMATION: 4HYP 4-Hydroxyproline
<220> FEATURE:
<221> NAME/KEY: MISC_FEATURE
<222> LOCATION: (12)..(12)
<223> OTHER INFORMATION: 4HYP 4-Hydroxyproline
<220> FEATURE:
<221> NAME/KEY: MISC_FEATURE
<222> LOCATION: (15)..(15)
<223> OTHER INFORMATION: 4HYP 4-Hydroxyproline
<220> FEATURE:
<221> NAME/KEY: MISC_FEATURE
<222> LOCATION: (18)..(18)
<223> OTHER INFORMATION: 4HYP 4-Hydroxyproline
<220> FEATURE:
<221> NAME/KEY: MISC_FEATURE
<222> LOCATION: (21)..(21)
<223> OTHER INFORMATION: 4HYP 4-Hydroxyproline
```

```
<400> SEQUENCE: 2

Gly Pro Xaa Gly Pro Xaa Gly Pro Xaa Gly Pro Xaa Gly Pro Xaa Gly
1               5                   10                  15

Pro Xaa Gly Pro Xaa
            20

<210> SEQ ID NO 3
<211> LENGTH: 9
<212> TYPE: PRT
<213> ORGANISM: Homo sapiens

<400> SEQUENCE: 3

Cys Asn Pro Arg Gly Asp Tyr Arg Cys
1               5
```